United States Patent
Xu et al.

(10) Patent No.: US 11,203,772 B2
(45) Date of Patent: Dec. 21, 2021

(54) CHEMOENZYMATIC SYNTHESIS OF STRUCTURALLY HOMOGENEOUS ULTRA-LOW MOLECULAR WEIGHT HEPARINS

(75) Inventors: Yongmei Xu, Durham, NC (US); Jian Liu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/996,930

(22) PCT Filed: Dec. 22, 2011

(86) PCT No.: PCT/US2011/066843
§ 371 (c)(1),
(2), (4) Date: Jul. 18, 2013

(87) PCT Pub. No.: WO2012/088416
PCT Pub. Date: Jun. 28, 2012

(65) Prior Publication Data
US 2013/0296540 A1 Nov. 7, 2013

Related U.S. Application Data

(60) Provisional application No. 61/426,921, filed on Dec. 23, 2010.

(51) Int. Cl.
| | | |
|---|---|---|
| *C12P 19/18* | (2006.01) |
| *C12P 19/26* | (2006.01) |
| *C08B 37/00* | (2006.01) |
| *C12P 19/04* | (2006.01) |
| *C12N 9/10* | (2006.01) |

(52) U.S. Cl.
CPC .......... *C12P 19/18* (2013.01); *C08B 37/0075* (2013.01); *C12N 9/1051* (2013.01); *C12P 19/04* (2013.01); *C12P 19/26* (2013.01)

(58) Field of Classification Search
CPC .......... C12P 19/04; C12P 19/18; C12P 19/26; C08B 37/0075
See application file for complete search history.

(56) References Cited

U.S. PATENT DOCUMENTS

| | | | |
|---|---|---|---|
| 4,865,870 A | 9/1989 | Hu et al. |
| 5,543,403 A | 8/1996 | Petitou et al. |
| 5,817,487 A | 10/1998 | Kobayashi et al. |
| 5,834,282 A | 11/1998 | Habuchi et al. |
| 5,935,824 A | 8/1999 | Sgarlato |
| 6,255,088 B1 | 7/2001 | Wong et al. |
| 6,861,254 B1 | 3/2005 | Rosenberg et al. |
| 7,531,338 B2 | 5/2009 | Liu |
| 9,951,149 B2 | 4/2018 | Liu et al. |
| 2003/0083294 A1 | 5/2003 | Sullenger |
| 2003/0099967 A1 | 5/2003 | Deangells |
| 2004/0191870 A1 | 9/2004 | Rosenberg et al. |
| 2005/0101532 A1 | 5/2005 | Yang et al. |
| 2005/0255562 A1 | 11/2005 | Rosenberg et al. |
| 2006/0165673 A1 | 7/2006 | Liu |
| 2006/0172931 A1 | 8/2006 | San Antonio et al. |
| 2008/0109236 A1* | 5/2008 | DeAngelis ........... A61K 39/102 435/188.5 |
| 2009/0035787 A1 | 2/2009 | Liu |
| 2009/0197308 A1 | 8/2009 | Liu |
| 2010/0125052 A1 | 5/2010 | Lu et al. |
| 2010/0305022 A1 | 12/2010 | Shriver |
| 2011/0054236 A1 | 3/2011 | Yang et al. |
| 2012/0308546 A1 | 12/2012 | Kizhakkedathu et al. |
| 2012/0322114 A1 | 12/2012 | Liu et al. |
| 2012/0322760 A1 | 12/2012 | Fier et al. |
| 2013/0022647 A1 | 1/2013 | Kizhakkedathu et al. |
| 2016/0122446 A1 | 5/2016 | Liu et al. |

FOREIGN PATENT DOCUMENTS

| | | |
|---|---|---|
| EP | 0 394 971 | 10/1990 |
| EP | 0 565 863 | 10/1993 |
| JP | 6670235 | 3/2020 |
| WO | WO 96/14425 | 5/1996 |
| WO | WO2003018598 | 3/2003 |
| WO | WO 2004/005475 A2 | 1/2004 |
| WO | WO 2004/009642 | 1/2004 |
| WO | WO 2004-017910 | 3/2004 |
| WO | WO 2006/124801 | 11/2006 |
| WO | WO 2012/088416 | 6/2012 |
| WO | WO2012/088416 | 6/2012 |
| WO | WO 2012/116048 | 8/2012 |
| WO | WO2014/204929 | 12/2014 |
| ZA | 2014800444299 | 5/2021 |

OTHER PUBLICATIONS

Vives, Romain R. et al., Biochem. J., "Sequence analysis of heparan sulphate and heparin oligosaccharides", 1999, vol. 339, pp. 767-773.*
Brown et al., Drug Research, "Cardenolide analogues. 11. Improved method for the use of Fetizon's reagent in the synthesis of cardiac glycosides", 1981, vol. 31, No. 7, pp. 1059-1064.*
Chen, Miao, Towards De Novo Synthesis of Structure-Defined Oligosaccharides with Heparan Sulfate Biosynthetic Enzymes, PhD dissertation, Date Created: Aug. 2008; Date Deposited: Oct. 11, 2010.*
Sala, R. F. et al., Carbohydrate Research, "UDP-N-trifluoroacetylglucosamine as an alternative substrate in N-acetylglucosaminyltransferase reactions", 1998, vol. 306, pp. 127-136.*
STN record for Chen et al., dissertation, "Towards de novo synthesis of structure-defined oligosaccharides with heparan sulfate biosynthetic enzymes", entered into STN: Apr. 20, 2009.*
Liu, J. et al., Royal Society of Chemistry, "Chemoenzymatic synthesis of heparan sulfate and heparin", 2014, vol. 31, pp. 1676-1685 (Year: 2014).*

(Continued)

*Primary Examiner* — Bahar Craigo
(74) *Attorney, Agent, or Firm* — Jenkins, Wilson, Taylor & Hunt, P.A.

(57) ABSTRACT

Methods for preparing synthetic heparins are provided. Synthetic heparin compounds, including ultralow molecular weight heparin compounds are provided. Also provided are methods of chemoenzymatically synthesizing structurally homogeneous ultra-low molecular weight heparins. Heparin compounds provided herein can have anticoagulant activity.

3 Claims, 13 Drawing Sheets

(56) References Cited

OTHER PUBLICATIONS

Peterson, S. et al., Natural Product Reports, "Design of biologically active heparan sulfate and heparin using an enzyme-based approach", 2009, vol. 26, pp. 610-627 (Year: 2009).*
Rosenberg, R. et al., The Journal of Biological Chemistry, "Chemoenzymatic Synthesis of Classic and Non-classical Anticoagulant Heparan Sulfate Polysaccharides", 2003, vol. 278, No. 52, pp. 52613-52621 (Year: 2003).*
Aikawa et al. (1999) J. Biol. Chem., 274, 2690.
Aikawa J.-L, et al., (2001) J. Biol. Chem., 276, 5876-5882.
Balagurunathan, K., et al. (2003) Nat. Biotechnol. 21, 1343-1346.
Baleux et al. (2009) Nat. Chem. Biol., 5, 743-748.
Bitter et al. (1962) Anal. Biochem. 4, 330-334.
Bowman et al. (1999) Chem. Biol. 6, R9-R22.
Burkart, et al. (2000) J. Org. Chem., 65, 5565-5574.
Carfi A., et al., (2001) Mol. Cell, 8, 169-179.
Chen, J., et al. (2005) J. Biol. Chem., 280, 42817-42825.
Chen, J., et al., (2007), Chem. Biol., 14, 986-993.
Chen, M., et al. (2006) Biochemistry, 45, 12358-12365.
Dooley (1998) Chemico-Biol. Interact., 109, 29.
Duncan et al. (2004), Biochim. Biophys. Acta 1671, 34-43.
Edens, R.E., et al., (1992) J. Pharm. Sci., 81, 823-827.
Esko and Lindahl (2001) J. Clin. Invest., 108, 169-173.
Esko and Selleck (2002) Annu. Rev. Biochem., 71, 435-471.
Falany (1997) FASEB J., 11, 1-2.
Feyerabend et al. (2006) Nat. Chem. Biol., 2, 195-196.
Fukuta et al. (1998) Biochim. Biophys. Act., 1399, 57.
GENBANK Accession No. AAC40135.
GENBANK Accession No. BAA89247.
GENBANK Accession No. NP_005105.
GENBANK Accession No. NP_006032.
GENBANK Accession No. NP_006033.
GENBANK Accession No. NP_056633.
GENBANK Accession No. NP_056635.
Guerrini et al. (2008) Nat. Biotechnol., 26, 669-675.
Habuchi et al. (1998) J. Biol Chem., 273, 9208.
Habuchi et al. (2000) J. Biol. Chem., 275, 2859-2868.
Hirsch et al. (2004) CHEST, vol. 126, p. 188S-203S.
Hirsh et al. (2007) Circulation, 116, 552-560.
International Preliminary Report on Patentability corresponding to International Application No. PCT/US2011/066843 dated Jul. 4, 2013.
Kakkar et al. (2004) J. Clin. Oncol., vol. 22, pp. 1944-1948.
Krummenacher, C. et al. (1999) J. Virol., 73, 8127-8137.
Laurent et al. (1987) Biochem. J., vol. 175, pp. 691-701.
Lee and Lander (1991) Proc. Natl. Acad. Sci. USA, 88, 2768-2772.
Lindahl et al. (1998) J. Biol. Chem., 273, 24979-24982.
Lindahl, Li, Kusche-Gullbert, et al. (2005) J. Med. Chem., 48, 349-352.
Linhardt et al. (1999) Seminars in Thrombosis and Hemostasis, vol. 25, Suppl.3, pp. 5-16.
Linhardt, R.J. (2003) J. Med. Chem., 46, 2551-2564.
Liu and Pedersen (2007) Microbiol. Biotechnol., 74, 263-272.
Liu and Thorp (2002) Med. Res. Rev., 22, 1-25.
Liu et al. (1996) J. Biol. Chem., 271, 27072-27082.
Liu et al. (1999) J. Biol. Chem., 274, 38155-38162.
Liu et al. (2002) J. Biol. Chem., 277, 33456-33467.
Liu et al. (2009) Nat. Prod. Rep., 26, 313-321.
Liu et al. (2010) J. Biol. Chem., 285, 34240-34249.
Loganathan et al. (1990) Biochemistry, 29, 4362-4368.
Maccarana and Lindahl (1993) Glycobiology, 3, 271.
Martinez-Gonzalez and Rodriguez (2010) Expert Rev. Cardiovasc. Ther., 8, 625-634.
Mazany et al. (1998) Biochim. Biophys. Act., 1407, 92.
Mousa (2010), Meth. Mol. Biol., 663, 1-28.
Mousa (2010), Meth. Mol. Biol., 663, 29-107.
Mousa S.A. in Drug Discovery and Evaluation: Pharmacological Assays (ed. Vogel, H.), 393-456 (Springer-Verlag Berlin, Heidelberg, New York, 2008).
Nastuk et al. (1998) J. Neuroscience, 18, 7167.
Noti and Seeberger, (2005) Chemistry & Biology, 12, 731-756.
Ong et al. (1998) J. Biol. Chem., 273, 5190.
Ouyang et al. (1998), J. Biol. Chem., 273, 24770.
Petitou and van Boeckel (2004) Angew. Chem. Int. Ed., 43, 3118-3133.
Saeki et al. (1998) J. Biochem., 124, 55.
Shriver et al. (2004) Nat. Rev. Drug Discov., 3, 863-873.
Shukla and Spear (2001) J. Clin. Invest., 108, 503-510.
Shukla et al. (1999) Cell, 99, 13-22.
Shworak et al. (1997) J. Biol. Chem., 272, 28008-28019.
Sismey-Ragatz, et al. (2007) J. Biol. Chem., 282, 28321-28327.
Tohu et al. (2004) Clin. Appl. Thrombos Hemostas, 10, 301-309.
Uchimura et al. (1998) J. Biol. Chem., 273, 22577.
Wang et al. (2010) Biotechnol. Bioeng 107, 968-977.
Weitz (2010) Thromb. Res., 125 (Suppl 2), S30-S35.
Weitz and Linkins, (2007) Expert Opin. Investig. Drugs, 16, 271-282.1.
Willis et al. (1998) J. Virol. 72, 5938-5947.
WuDunn and Spear (1989) J. Virol. 63, 52-58.
Xu et al. (2008) Nat. Chem. Biol., 4, 200-202.
Xu et al. (2011) Science,vol. 334, 498-501.
Yoshinari et al. (1998) J. Biochem. 123, 740.
Zhang et al. (2001) J. Biol. Chem. 276,42311-42321.
Zhang et al. (2008) J. Am. Chem. Soc., 130, 12998-13007.
Zhou et al. "Expression of heparin sulfate sulfotransferases in Kluyveromyces lactis and preparation of 3'-phsphoadenosie-5'-phosphosulfate" (2011) Glycobiology, 21(6), 771-780.
Atha et al., "Contribution of Monosaccharide Residues in Heparin Binding to Antithrombin III," Biochemistry, vol. 24, pp. 6723-6729 (1985).
Avci et al., "Synthetic oligosaccharides as heparin-mimetics displaying anticoagulant properties," Curr. Pharm. Des., vol. 9, pp. 2323-2335 (2003).
Balagurunathan et al., Chemoenzymatic Synthesis of Classical and Non-classical Anticoagulant Heparan Sulfate Polysaccharide, J. Biol. Chem., vol. 278, pp. 52613-52621 (2003).
Bjornsson, Simultaneous Preparation and Quantitation of Proteoglycans by Preciptation with Alcian Blue, Anal. Biochem., vol. 210, pp. 282-291 (1993).
Broun et al., "Catalytic plasticity of fatty acid modification enzymes underlying chemical diversity of plant lipids," Science, vol. 282, pp. 1315-1317 (1998).
Cai et al., "Towards the chemoenzymatic synthesis of heparan sulfate oligosaccharides: Oxidative cleavage of p-nitrophenyl group with ceric ammonium salts," Tetra. Lett., vol. 54, No. 33, pp. 4471-1474 (2013).
Casu et al., Heparin-like compounds prepared by chemical modification of capsular polysaccharide from *E. coli* K5, Carbohydrate Research vol. 263, pp. 271-228 (1994).
Chen et al., "Biosynthesis of 3-O-sulfated heparan sulfate: unique substrate specificity of heparan sulfate 3-O-sulfotransferase isoform 5," Glycobiology, vol. 13, No. 11, pp. 785-794 (Nov. 2003).
Chen et al., "Tyrosine-Ester Sulfotransferase from Rat Liver: Bacterial Expression and Identificationn," Protein Expression Purif., vol. 3, pp. 421-426 (1992).
Conrad, Heparin-Binding Proteins, J. of Medicinal Chemistry, vol. 42, No. 4, pp. 777-778 (1998).
Copeland et al., "Using a 3-O-Sulfated Heparin Octasaccharide to Inhibit the Entry of Herpes Simplex Virus Type 1 " Biochemistry, vol. 47, pp. 5774-5783 (2008).
Communication of the extended European search report corresponding to European Application No. 14812890.3 dated Dec. 21, 2016.
Communication of European publication number and information on the application of Article 67(3) EPC corresponding to European Application No. 14812890.3 dated Mar. 31, 2016.
Crowther et al., "Mechanisms responsible for the failure of protamine to inactivate low-molecular-weight heparin," British Journal of Hematology, vol. 116, pp. 178-186 (2002).
Das et al., "Synthesis of Conformationally Locked I-lduronic Acid Derivatives: Direct Evidence for a Critical Role of the Skew-Boat 2S0 Conformer in the Activation of Antithrombin by Heparin," Chem. Eur. J., vol. 7, No. 22, pp. 4821-4834 (2001).

(56) References Cited

OTHER PUBLICATIONS

Davenport, "Review article: Low-molecular-weight heparin as an alternative anticoagulant to unfractionated heparin for routine outpatient haemodialysis treatments," Nephrology, vol. 14, pp. 456-461 (2009).
Dementiev et al., "The ternary complex of antithrombin-anhydrothrombin-heparin reveals the basis of inhibitor specificity," Nat. Struct. Biol., vol. 11, pp. 867-863 (2004).
Dou et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).
Edavettal et al.,, "Crystal Structure and Mutational Analysis of Heparan Sulfate 3-O-Sulfotransferase Isoform 1 " J. Biol. Chem., vol. 279, No. 24, pp. 25789-25797 (Jun. 11, 2004).
Fuster et al., The sweet and sour of cancer: glycans as novel therapeutic targets, Nat. Rev. Cancer, vol. 5, No. 7, pp. 1-27 (Jul. 2005).
Gallagher, "Heparan sulfate: growth control with a restricted sequence menu," J. Clin. Invest., vol. 108, pp. 357-361 (2001).
Gama et al., "Sulfation patterns of glycosaminoglycans encode molecular recognition and activity," Nat. Chem. Biol., vol. 2, No. 9, pp. 467-473 (Sep. 2006).
Guimond et al.."Fibroblast growth factor receptor signaling is dictated by specific heparin sulphate saccharides," Curro. Biol., vol. 9, No. 22 pp. 1343-1346 (1999).
Guo et al., "Changes in substrate specificity of the recombinant form of phenol sulfotransferase IV (tyrosine-ester sulfotransferase)," Chem.-Biol. Interact., vol. 92, pp. 25-31 (1994).
Harris et al., Endocytic Function, Glycosaminoglycan Specificity, and Antibody Sensitivity of the Recombinant Human 190-kDa Hyaluronan Receptor for Endocytosis (Hare), J. Biol. Chern., vol. 279, No. 35, p. 36201-36209 (Aug. 27, 2004).
Hernaiz et al., "Enzymatic Modification of Heparan Sulfate on a Biochip Promotes Its Interaction with Antithrombin III," Biochem. Biophys. Res. Commun., vol. 276, pp. 292-297 (2000).
Holmborn et al., "Heparan Sulfate Synthesized by Mouse Embryonic Stem Cells Deficient in NDST1 and NDST2 Is 6-O-Sulfated but Contains No N-Sulfate Groups," J. Biol. Chem., vol. 279, No. 41, pp. 42355-42358 (2004).
Ibrahimi et al., "Kinetic Model for FGF, FGFR, and Proteoglycan Signal Transduction Complex Assembly," Biochemistr, vol. 43, pp. 4724-4730 (2004).
International Preliminary Report on Patentability corresponding to International Application No. PCT/US2014/042683 dated Dec. 30, 2015.
International Search Report corresponding to International Application No. PCT/US2014/042683 dated Oct. 9, 2014.
Jemth et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).
Kakuta et al., "Heparan sulphate N-sulphotransferase activity: reaction mechanism and substrate recognition," Biochem. Soc. Trans., vol. 31 (pt2), pp. 331-334 (2003).
Kisselev, L., "Polypeptide release factors in prokaryotes and eukaryotes: same function, different structure," Structure, vol. 10, pp. 8-9 (2002).
Kreuger et al., Interactions between heparan sulfate and proteins: the concept of specificity, J. Cell Biol., vol. 174, No. 3, pp. 323-327 (Jul. 31, 2006).
Kuberan et al., "Rapid Two-Step Synthesis of Mitrin from Heparosan: A Replacement for Heparin," J. Am. Chem. Soc., vol. 125, p. 12424-12425 (2003).
Ledin et al., "Heparan Sulfate Structure in Mice with Genetically Modified Heparan Sulfate Production," J. Biol. Chem., vol. 279, No. 41, pp. 42732-42741 (2004).
Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).
Lin et al., "Colorimetric Determination of the Purity of 39-Phospho Adenosine 59-Phosphosulfate and Natural Abundance of 39-Phospho Adenosine 59-Phosphate at Picomole Quantities," Anal. Biochem., vol. 264, pp. 111-117 (1998).
Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).
Liu et al., "Expression of Heparan Sulfate D-Glucosaminyl 3-O-Sulfoliansferase Isoforms Reveals Novel Substrate Specificities," The Journal of Biological Chemistry, vol. 274, No. 8, pp. 5185-5192 (Feb. 19, 1999).
Mackman, "Triggers, targets and treatments for thrombosis," Nature, vol. 451, No. 21, pp. 914-918 (Feb. 21, 2008).
Marshall et al., "Control of Activity through Oxidative Modification at the Conserved Residue Cys66 of Aryl Sulfotransferase IV," J. Biol. Chem., vol. 272, No. 14, pp. 9153-9160 (Apr. 14, 1997).
Marshall et al., "A review of the effects of manipulation of the cysteine residues of rat aryl sulfotransferase IV," Chem. Biol. Interact., vol. 109, pp. 107-116 (1998).
Moon et al., "Structural Analysis of the Sulfotransferase (3-O-Sulfotransferase Isoform 3) Involved in the Biosynthesis of an Entry Receptor for Herpes Simplex Virus 1," J. Biol. Chem., vol. 279, No. 43, pp. 45185-45193(2004).
Moon et al., "Dissecting the substrate recognition of 3-0-suflotransferase for the biosynthesis of anticoagulant heparin," Proceedings of the National Academy of Sciences, vol. 109, No. 14, pp. 5265-5270 (2012).
Munoz et al., "Enzymatic synthesis of heparin related polysaccharides on sensor chips: Rapid screening of heparin-protein interactions," Biochemical and Biophysical Research Communications, Academic Press Inc., Orlando, FL, US, vol. 339, No. 2, pp. 597-602 (Jan. 13, 2006).
Nicola et al., Structure-Function Analysis of Soluble Forms of Herpes Simplex Virus Glycoprotein D., J. Virol., vol. 70, No. 6, pp. 3815-3822 (1996).
Notification Concerning of Transmittal of International Preliminary Report on Patentability for International Application No. PCT/US2006/018778 (dated Nov. 22, 2007).
Notification of Transmittal of the International Search Report and the Written Opinion of the International Searching Authority, or the Declaration for International Application No. PCT/US06/18778 (dated Feb. 21, 2007).
Notification of Transmittal of the International Search Report and the Written Opinion of the International Searching Authority, or the Declaration corresponding to International Application No. PCT/US2008/008945 (dated Feb. 20, 2009).
Office Action corresponding to U.S. Appl. No. 12/178,434 dated Oct. 28, 2011.
Office Action corresponding to U.S. Appl. No. 12/178,434 dated Apr. 19, 2011.
Office Action corresponding to U.S. Appl. No. 12/178,434 dated Jan. 26, 2011.
Official Action corresponding to U.S. Appl. No. 11/920,319 dated Apr. 28, 2010.
Official Action corresponding to U.S. Appl. No. 14/898,865 dated Mar. 23, 2017.
Ornitz et al., "Receptor Specificity of the Fibroblast Growth Factor Family," J. Biol. Chem., vol. 271, No. 25, pp. 15292-15297 (1996).
Ozawa et al., "Nucleotide sequence of a full-length cDNA (PST-1) for aryl sulfotransferase from rat liver," Nucleic Acids Res., vol. 18, No. 13, p. 4001 (1990).
Pempe, et al., "Probing Structural Selectivity of Synthetic Heparin Binding to Stabilin Protein Receptors," Journal of Biol. Chem., vol. 287, No. 25, pp. 20774-20783 (Jun. 15, 2012).
Petitou et al., "Synthesis of thrombin-inhibiting heparin mimetics without side effects." Nature, vol. 398, pp. 417-422 (Apr. 1, 1999).
Pinhal et al., "Enzyme interactions in heparan sulfate biosynthesis: Uronosyl 5-epimerase and 2-O-sulfotransferase interact in vivo.," Proc. Natl. Acad. Sci. U. S. A., vol. 98, No. 23, pp. 12984-12989 (Nov. 6, 2001).

(56) References Cited

OTHER PUBLICATIONS

Pye et al., "Heparan Sulfate Oligosaccharides Require 6-O-Sulfation for Promotion of Basic Fibroblast Growth Factor Mitogenic Activity," J. Biol. Chem., vol. 273, No. 36, pp. 22936-22942 (Sep. 4, 1998).
Razi et al., "Structural and functional properties of heparin analogues obtained by chemical sulphation of *Escherichia coli* K5 capsular polysaccharide," Biochem. J., vol. 389, pp. 465-472 (1995).
Saribas et al., "Production of N-sulfated 1-38 polysaccharides using yeast-expressed N-deacetylase/N-sulfotransferase-1 (NDST-I)," Glycobiology, vol. 14, pp. 1217-1228 (2004).
Sasisekharan et al., "Roles of Heparan-Sulphate Glycosaminoglycans in Cancer," Nat. Rev. Cancer, vol. 2, pp. 521-528 (Jul. 2002).
Schroeder et al., "Protamine neutralization of low molecular weight heparins and their oligosaccharide components," Anal Bioanal Chem, vol. 399, pp. 763-771 (2011).
Sheng et al., "Influenced of Phenylalanines 77 and 138 on the Stereospecifity of Aryl Sulfotransferase IV," Drug Metabol. Dispos., vol. 32, No. 5, pp. 559-565 (2004).
Sheng et al., "The Dominating Role of N-Deacetylase/N-Sulfotransferase 1 in Forming Domain Structures in Heparan Sulfate," The Journal of Biological Chemistry, vol. 286, No. 22, pp. 19768-19776 (Jun. 3, 2011).
Shively et al., "Formation of Anhydrosugars in the Chemical Depolymerization of Heparin," Biochemistry, vol. 15, No. 18, pp. 3932-3942 (1976).
Smeds et al., "Substrate specificities of mouse heparan sulphate glucosaminyl 6-O-sulphotransferases," Biochem. J, vol. 372, pp. 371-380 (2003).
Sundaram, M. et al., "Rational design of low-molecular weight heparins with improved in vivo activity," Proc. Natl. Acad. Sci., vol. 100, No. 2, pp. 651-656 (Jan. 21, 2003).
Vann et al., "The Structure of the Capsular Polysaccharide (K5 Antigen) of Urinary-Tract-Infective *Escherichia coli* 010 : K5 : H4 A Polymer Similar to Desulfo-Heparin," Eur. J. Biochem, vol. 116, pp. 359-364 (1981).
Wishart et al., "A single mutation converts a novel phosphotyosine binding domain into a dual-specificity phosphatase," J. Biol. Chem., vol. 270, No. 45, pp. 26782-26785 (1995).
Witkowski et al., "Conversion of b-ketoacyl synthase to a Malonyl Decarboxylase by replacement of the active cysteine with glutamine," Biochemistry, vol. 38, pp. 11643-11650 (1999).
Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol. 277, No. 40, pp. 37912-37919 (2002).
Xu et al., "Characterization of heparan sulphate 3-O-sulphotransferase isoform 6 and its role in assisting the entry of herpes simplex virus type 1," Biochem. J., vol. 385, pp. 451-459 (2005).
Xu, et al., "Homogeneous low-molecular-weight heparins with reversible anticoagulant activity," Nat Chem Biol., vol. 10, pp. 248-252 (2014).
Yang et al. Effects of 3'-phosphoadenosine 5'-phosphate on the activity and folding of phenol sulfotransferase. Chem.-Biol. Interact. 109: 129-135 (1998).
Yang et al., "Two Phenol Sulfotransferase Species from One cDNA: Nature of the Differences," Protein Expression Purif, vol. 8, pp. 423-429 (1996).
Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).
Zhao et al. "Enzymatic route to preparative-scale synthesis of UDP-GlcNAc/GalNAc, their analogues and GDP-fucose," Nat. Protoc., vol. 5, No. 4, pp. 636-646 (2010).
Notice of Allowance and Interview Summary corresponding to U.S. Appl. No. 14/898,865 dated Dec. 15, 2017.
Supplemental Notice of Allowability and Interview Summary corresponding to U.S. Appl. No. 14/898,865 dated Jan. 12, 2018.
Office Action corresponding to Chinese Patent Application No. 201480044429.9 dated Apr. 9, 2019.
Office Action corresponding to Chinese Patent Application No. 201480044429.9 dated Aug. 30, 2018.
Office Action corresponding to Japanese Patent Application No. 2016-521505 dated Jul. 19, 2018.
Office Action corresponding to Japanese Patent Application No. 2016-521505 dated Jun. 21, 2019.
Office Action corresponding to European Patent Application No. 11849994.6 dated May 24, 2018.
Office Action corresponding to European Patent Application No. 11849994.6 dated Jan. 22, 2020.
Decision to Grant corresponding to Japanese Patent Application No. 2016521505 dated Feb. 3, 2020.
Office Action corresponding to Chinese Patent Application No. 201480044429.9 dated Mar. 3, 2020.
Intention to Grant corresponding to European Patent Application No. 11849994.6 dated Apr. 7, 2021.
Kuberan et al., "Enzymatic synthesis of antithrombin III-binding heparan sulfate pentasaccharide," Nature Biotechnology, vol. 21, No. 11, 1343-1346 (Nov. 2003).
Liu et al., "Enzymatic Placement of 6-O-Sulfo Groups in Heparan Sulfate," Biochemistry 2011, 50, 4382-4391.
Office Action corresponding to European Patent Application No. 11849994.6 dated Jun. 23, 2020.
Intention to Grant corresponding to European Patent Application No. 11849994.6 dated Sep. 1, 2021.
Intention to Grant corresponding to European Patent Application No. 14812890.3 dated Oct. 27, 2021.

\* cited by examiner

CHEMOENZYMATIC SYNTHESIS OF STRUCTURALLY HOMOGENEOUS ULTRA-LOW MOLECULAR WEIGHT HEPARINS

CROSS REFERENCE TO RELATED APPLICATION

The presently disclosed subject matter claims the benefit of U.S. Provisional Patent Application Ser. No. 61/426,921, filed Dec. 23, 2010, the disclosure of which is incorporated herein by reference in its entirety.

GRANT STATEMENT

This invention was made with government support under Grant Nos. HL094463 and HL096972 awarded by the National Institutes of Health. The government has certain rights in the invention.

TECHNICAL FIELD

The subject matter disclosed herein relates generally to synthesis of heparin compounds. More particularly, the subject matter disclosed herein relates to chemoenzymatic synthesis of structurally homogeneous ultra-low molecular weight heparins.

BACKGROUND

Heparan sulfate (HS) is a ubiquitous component of the cell surface and extracellular matrix. It regulates a wide range of physiologic and pathophysiologic functions, including embryonic development and blood coagulation, and can facilitate viral infection (Esko and Selleck (2002) *Annu. Rev. Biochem.* 71, 435-471; Liu and Thorp (2002) *Med. Res. Rev.* 22, 1-25). HS exerts its biological effects by interacting with the specific proteins involved in a given process (Capila and Lindhardt (2002) *Angew. Chem. Int Ed.* 41, 390-412). HS is a highly charged polysaccharide comprising 1→4-linked glucosamine and glucuronic/iduronic acid units that contain both N- and O-sulfo groups. Unique saccharide sequences within HS can determine the specificity of the binding of HS to its target proteins (Linhardt (2003) *J. Med. Chem.* 46, 2551-2564). Heparin, a specialized form of HS, is a commonly used anticoagulant drug. Thus, new methods for the synthesis of heparin compounds and HS attract considerable interest for those developing anticoagulant and other HS-related drugs having improved pharmacological effects.

Heparin has been successfully used as an anticoagulant drug for over 50 years (Mackman, 2008). It is currently marketed in three forms: unfractionated (UF) heparin ($MW_{avg}$~14000 Da); low molecular weight (LMW) heparin ($MW_{avg}$18 6000 Da); and the synthetic ULMW heparin pentasaccharide ARIXTRA® (MW 1508.3 Da). UF heparin is used in surgery and kidney dialysis due to its relatively short half-life and its safety for renal impaired patients (Hirsh et al., 2007). LMW heparins and the ULMW heparin ARIXTRA®, introduced over a decade ago, have played an increasingly important role for preventing venous thrombosis among high risk patients (Tohu et al, 2004; Weitz, 2010) because of their more predictable anticoagulant dose, long half-lives and their reduced risk of osteoporosis (Weitz and Linkins, 2007). Recent research on LMW heparin has resulted in the European approval of Bemiparin sodium (Martinez-Gonzalez and Rodriguez, 2010), a second-generation LMW heparin, and the United States approval of a generic LMW heparin, M-Enoxaparin.

UF heparin is isolated from porcine intestine or bovine lung, and LMW heparins are prepared through the chemical or enzymatic degradation of this animal-sourced UF heparin. A worldwide outbreak of contaminated heparin has raised concerns over the reliability and safety of animal sourced heparins and LMW heparins (Guerrini et al., 2008; Liu et al., 2009). As a result, a cost-effective method for preparing new synthetic heparins is highly desirable (Peterson et al., 2009).

SUMMARY

In some embodiments, the presently disclosed subject matter provides a method of synthesizing a heparin compound comprising: providing a saccharide substrate; elongating the saccharide substrate to a saccharide of a desired or predetermined length; performing an epimerization reaction; and performing one or more sulfation reactions, whereby a heparin compound is synthesized. In some embodiments, the presently disclosed subject matter provides a method of synthesizing a heparin compound, comprising: providing a disaccharide substrate; elongating the disaccharide substrate to a tetrasaccharide; elongating the tetrasaccharide to a hexasaccharide or heptasaccharide, wherein the hexasaccharide or heptasaccharide comprises a N-sulfotransferase substrate residue; converting the N-sulfotransferase substrate residue on the hexasaccharide or heptasaccharide to a N-sulfo glucosamine (GlcNS) residue; performing an epimerization reaction; and performing one or more sulfation reactions selected from the group consisting of a 2-O-sulfation reaction, a 6-O-sulfation reaction, a 3-O-sulfation reaction, and combinations thereof, whereby a heparin compound is synthesized.

In some embodiments, the elongation step comprises employing a glycosyl transferase. In some embodiments, the glycosyl transferase is selected from the group consisting of N-acetyl glucosaminyl transferase of *E. coli* K5 (KfiA) and/or heparosan synthase-2 (pmHS2) from *Pasteurella multocida*. In some embodiments, the elongation step comprises employing one or more monosaccharides selected from the group consisting of: glucuronic acid (GlcUA), N-acetylated glucosamine (GlcNAc), and N-trifluoroacetyl glucosamine (GlcNTFA).

Still yet, in some embodiments, the N-sulfotransferase substrate residue on the hexasaccharide or heptasaccharide to a N-sulfo glucosamine (GlcNS) residue comprises employing N-sulfotransferase (NST) and 3'-phosphoadenosine 5'-phosphosulfate (PAPS). In some embodiments, the method further comprises employing triethylamine, $CH_3OH$, and/or $H_2O$ in one or more converting reactions.

In some embodiments, the epimerization reaction comprises employing $C_5$-epimerase ($C_5$-epi). In some embodiments, the sulfation reaction comprises employing 2-O-sulfotransferase (2-OST). In some embodiments, the sulfation reaction comprises employing 6-O-sulfotransferase (6-OST). In some embodiments, the sulfation reaction comprises employing 3-O-sulfotransferase (3-OST).

In another aspect, the disclosed methods can further comprise elongating a hexasaccharide to a heptasaccharide using a glycosyl transferase. In some aspects, the glycosyl transferase is N-acetyl glucosaminyl transferase of *E. coli* K5 (KfiA).

In another aspect, the N-sulfotransferase substrate residue is a N-trifluoroacetyl glucosamine (GlcNTFA) residue.

Still yet, in some embodiments, the disclosed methods of synthesizing heparin compounds have a yield of greater than 30%. In some aspects, the disclosed methods have a recovery yield about 400-fold higher than methods of chemically synthesizing heparin.

Also provided herein are heparin compounds synthesized according to the disclosed methods. In some aspects, the heparin compounds have a molecular weight ranging from 1500 to 3000 daltons (Da). In some aspects, the heparin compounds have anticoagulant activity. In some aspects, the heparin compounds have binding affinity to antithrombin ranging from about 3 to about 12 nM. In some aspects, the heparin compounds have anti-Xa activity ranging from about 1 to about 5 nM $IC_{50}$. In some aspects, the heparin compounds have anti-Xa activity in the presence of platelet factor 4.

In some aspects, the presently disclosed subject matter provides a method of synthesizing a heparin compound, comprising: providing a disaccharide substrate; elongating the disaccharide substrate to a tetrasaccharide using enzymes N-acetyl glucosaminyl transferase and heparosan synthase-2, and substrates glucuronic acid (GlcUA) and N-trifluoroacetyl glucosamine (GlcNTFA); elongating the tetrasaccharide to a heptasaccharide using enzymes N-acetyl glucosaminyl transferase and heparosan synthase-2, and substrates glucuronic acid (GlcUA), N-trifluoroacetyl glucosamine (GlcNTFA), and N-acetylated glucosamine (GlcNAc); converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), triethylamine, $CH_3OH$, and $H_2O$; epimerizing the heptasaccharide using $C_5$-epimerase ($C_5$-epi); sulfating the heptasaccharide using 2-O-sulfotransferase (2-OST) and 3'-phosphoadenosine 5'-phosphosulfate (PAPS); sulfating the heptasaccharide using 6-O-sulfotransferase (6-OST) and 3'-phosphoadenosine 5'-phosphosulfate (PAPS); and sulfating the heptasaccharide using 3-O-sulfotransferase (3-OST) and 3'-phosphoadenosine 5'-phosphosulfate (PAPS); wherein a heparin compound is synthesized. Provided herein are heparin compounds produced by the above method.

In some embodiments, provided herein is a method of synthesizing a heparin compound, comprising: providing a disaccharide substrate; elongating the disaccharide substrate to a tetrasaccharide using enzymes N-acetyl glucosaminyl transferase and heparosan synthase-2, and substrates glucuronic acid (GlcUA) and N-trifluoroacetyl glucosamine (GlcNTFA); elongating the tetrasaccharide to a hexasaccharide using enzymes N-acetyl glucosaminyl transferase and heparosan synthase-2, and substrates glucuronic acid (GlcUA) and N-trifluoroacetyl glucosamine (GlcNTFA); converting N-trifluoroacetyl glucosamine (GlcNTFA) residue(s) on the hexasaccharide to N-sulfo glucosamine (GlcNS) residues using N-sulfotransferase (NST), 3'-phosphoadenosine 5'-phosphosulfate (PAPS), triethylamine, $CH_3OH$, and $H_2O$; elongating the hexasaccharide to a heptasaccharide using enzyme N-acetyl glucosaminyl transferase and substrate N-trifluoroacetyl glucosamine (GlcNTFA); epimerizing the heptasaccharide using $C_5$-epimerase ($C_5$-epi); sulfating the heptasaccharide using 2-O-sulfotransferase (2-OST) and 3'-phosphoadenosine 5'-phosphosulfate (PAPS); converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), triethylamine, $CH_3OH$, and $H_2O$; sulfating the heptasaccharide using 6-O-sulfotransferase (6-OST) and 3'-phosphoadenosine 5'-phosphosulfate (PAPS); and sulfating the heptasaccharide using 3-O-sulfotransferase (3-OST) and 3'-phosphoadenosine 5'-phosphosulfate (PAPS); wherein a heparin compound is synthesized. Provided herein are heparin compounds produced by the above method.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

FIG. 1A provides a schematic illustration of ULMW heparin construct 1. FIG. 1B provides a schematic illustration of ULMW heparin construct 2. In some embodiments, the synthesis of ULMW heparin constructs 1 and 2 can start from disaccharide 1, which can then be elongated to tetrasaccharide 2. In some embodiments, eight steps (steps a, b, c, d, e, f, g and h) can be employed to prepare ULMW heparin construct 1 from the elongated tetrasaccharide 2 (FIG. 1A). In some embodiments, steps d through h can be combined in sequential one-pot reaction format. In some embodiments, ten steps (steps a, b, d, e, a, f, d, e, g and h) can be employed to prepare ULMW heparin construct 2 (FIG. 1B) from the elongated to tetrasaccharide 2. The recovery yield at each purification step can be determined by parallel synthesis of the corresponding radioactively labeled oligosaccharide. "A", "B", "C", "D" and "E" below ULMW heparin construct 1 and ULMW heparin construct 2 in FIGS. 1A and 1B, and throughout the instant disclosure, are used only as references for each of the respective residues in the chemical structures and are not intended to be part of the chemical structures.

FIG. 2A shows the DEAE-HPLC profile of $^{35}$S-labeled product. FIG. 2B shows the ESI-MS spectrum of construct 1. FIG. 2C shows the 1D $^1$H NMR spectrum of ULMW construct 1. FIG. 2D shows the 2D correlation spectroscopy (COSY) spectrum of construct 1 with the peak assignments of the anomeric protons identified.

FIG. 3A shows the DEAE-HPLC profile of $^{35}$S-labeled product. FIG. 3B shows the ESI-MS spectrum of ULMW heparin construct 2. FIG. 3C shows the 1D $^1$H NMR spectrum of ULMW heparin construct 2. FIG. 3D shows the 2D COSY spectrum of ULMW heparin construct 2 with the peak assignments of the anomeric protons identified.

FIG. 4 does show the modification of the backbone polysaccharide using five enzymatic modification steps. The modification site at each step is highlighted in a hatched box.

Figure 2:
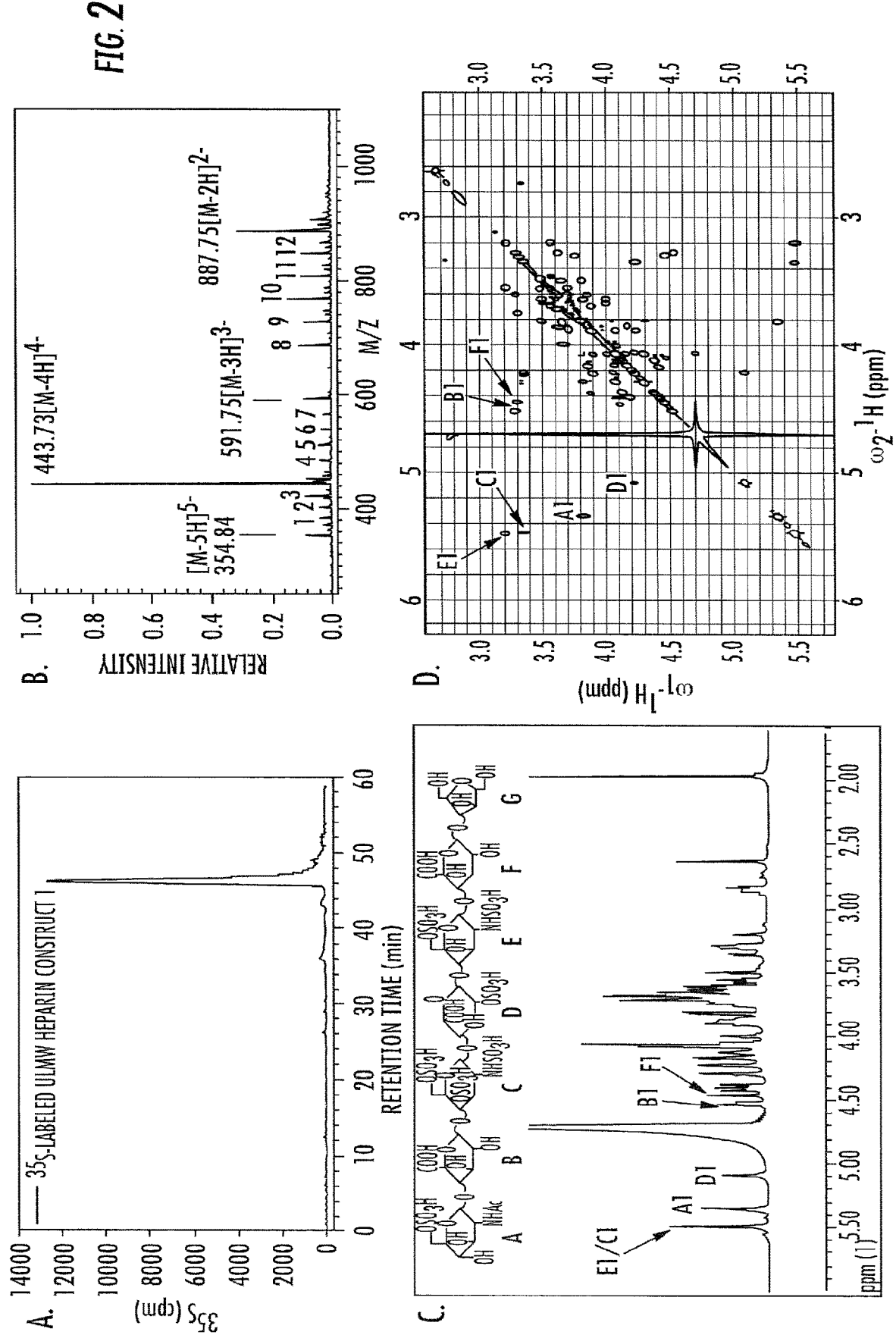
FIGS. 2A-2D depict the results of structural characterization analysis of ULMW heparin construct 1.

FIG. 5A shows the N—[$^{35}$S]sulfo labeled N-sulfated hetpasaccharide. The proposed structure is shown adjacent to FIG. 5A and at the top of the right column. FIG. 5B shows the 2-O—[$^{35}$S]sulfo labeled heptasaccharide after the incubation with a mixture of $C_5$-epi and 2-OST. The proposed structure of this intermediate is shown adjacent to FIG. 5B and in the middle of the right column. FIG. 5C shows the 6-O—[$^{35}$S]sulfo labeled heptasaccharide after modification by 6-OST-1 and 6-OST-3. The proposed structure of this intermediate is shown adjacent to FIG. 5C and at the bottom of the right column. The right column also indicates the reaction involved in the synthesis. The product after 6-O- sulfation was subjected to 3-O-sulfation to yield ULMW heparin construct 1. The elution profile of ULMW heparin construct 1 on DEAE-HPLC is shown in FIG. 2A. The modification site(s) at each step is highlighted in a hatched box.

Figure 3:
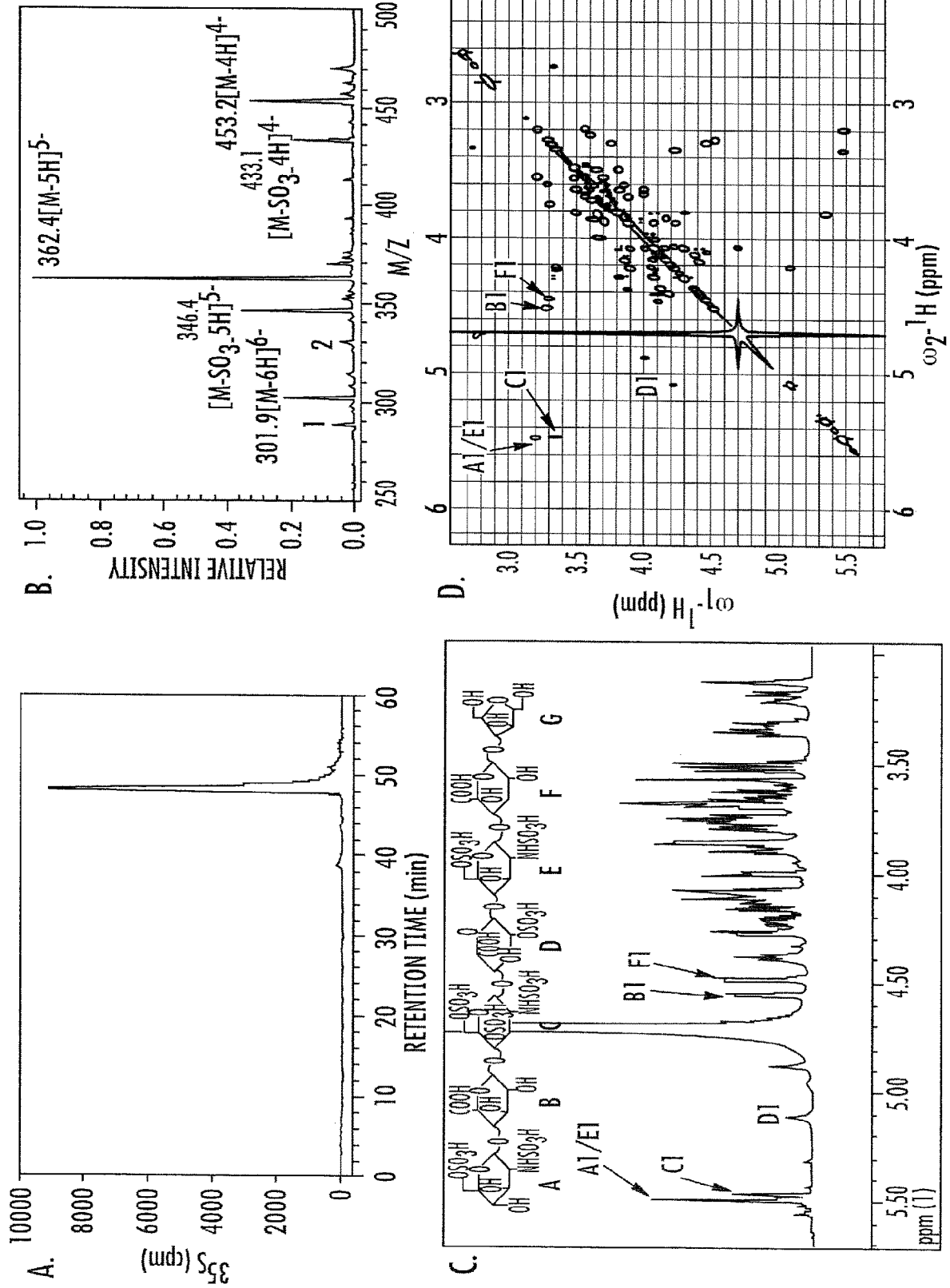
FIGS. 3A-3D depict the results of structural characterization analysis of ULMW heparin construct 2.
Figure 4:
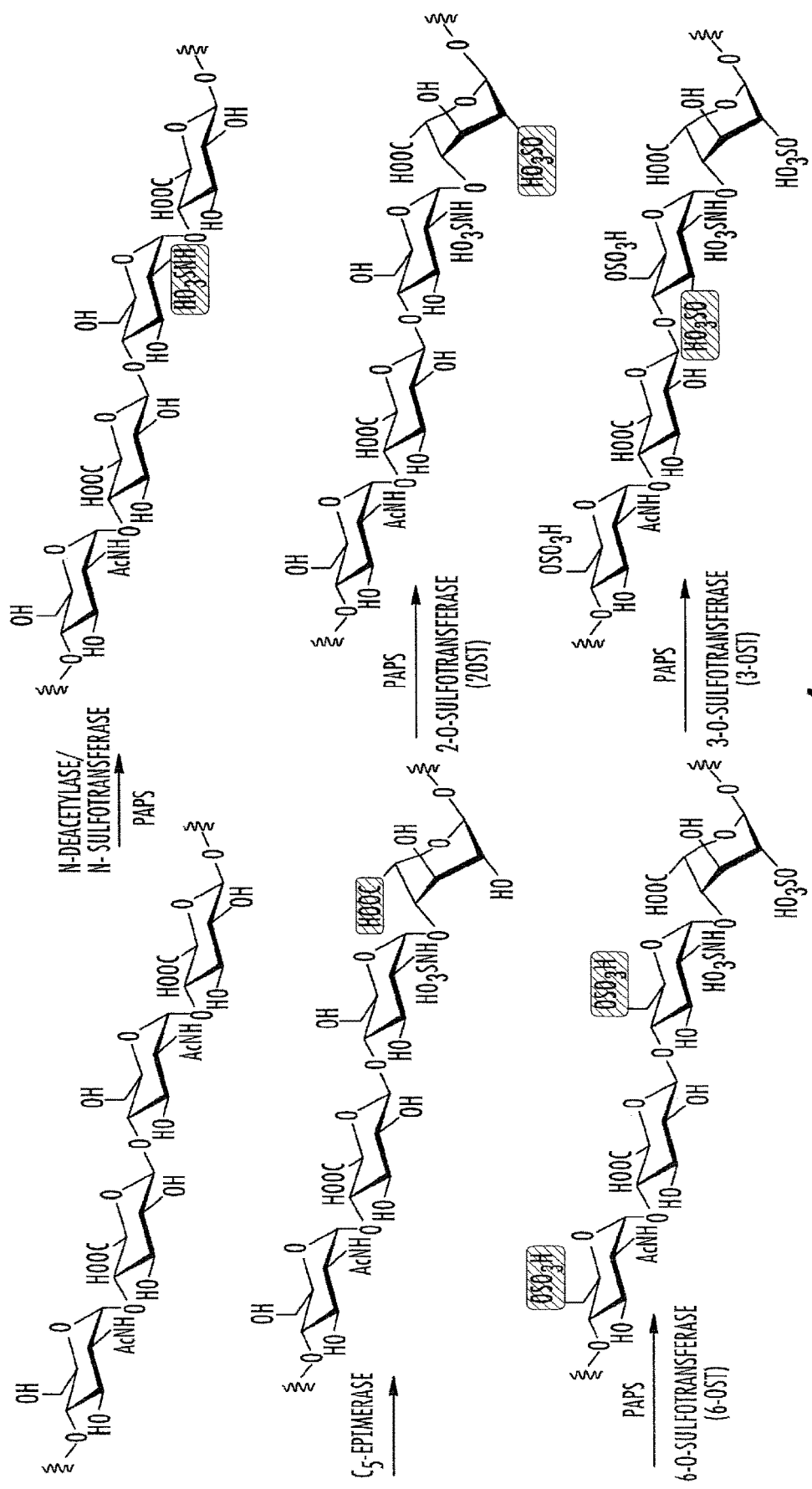
FIG. 4 is a schematic of a biosynthetic pathway of heparin and HS. Heparin and HS have similar disaccharide-repeating units, except heparin has a higher content of N-sulfo and O-sulfo groups and IdoUA. Portions of the biosynthetic pathway for heparin and HS is similar. The backbone synthesis that is catalyzed by HS polymerase is not shown.

FIGS. 6A and 6B depict DEAE-HPLC profiles of $^{35}$S-labeled intermediates during the preparation of ULMW heparin construct 2. FIG. 6A shows the DEAE-HPLC profile of N—[$^{35}$S]sulfo labeled heptasaccharide. The proposed structure is shown adjacent to FIG. 6A and at the top of the right column. FIG. 6B shows the 6-O—[$^{35}$S]sulfo labeled heptasaccharide after modification by 6-OST-1 and 6-OST-3. The proposed structure is shown adjacent to FIG. 6B and on the bottom of the right column. The product after 6-O-sulfation was subjected to 3-O-sulfation to yield ULMW heparin construct 2. The elution profile of ULMW heparin construct 2 on DEAE-HPLC is shown in FIG. 3A. The modification site(s) at each step is highlighted in a hatched box.

Figure 7:
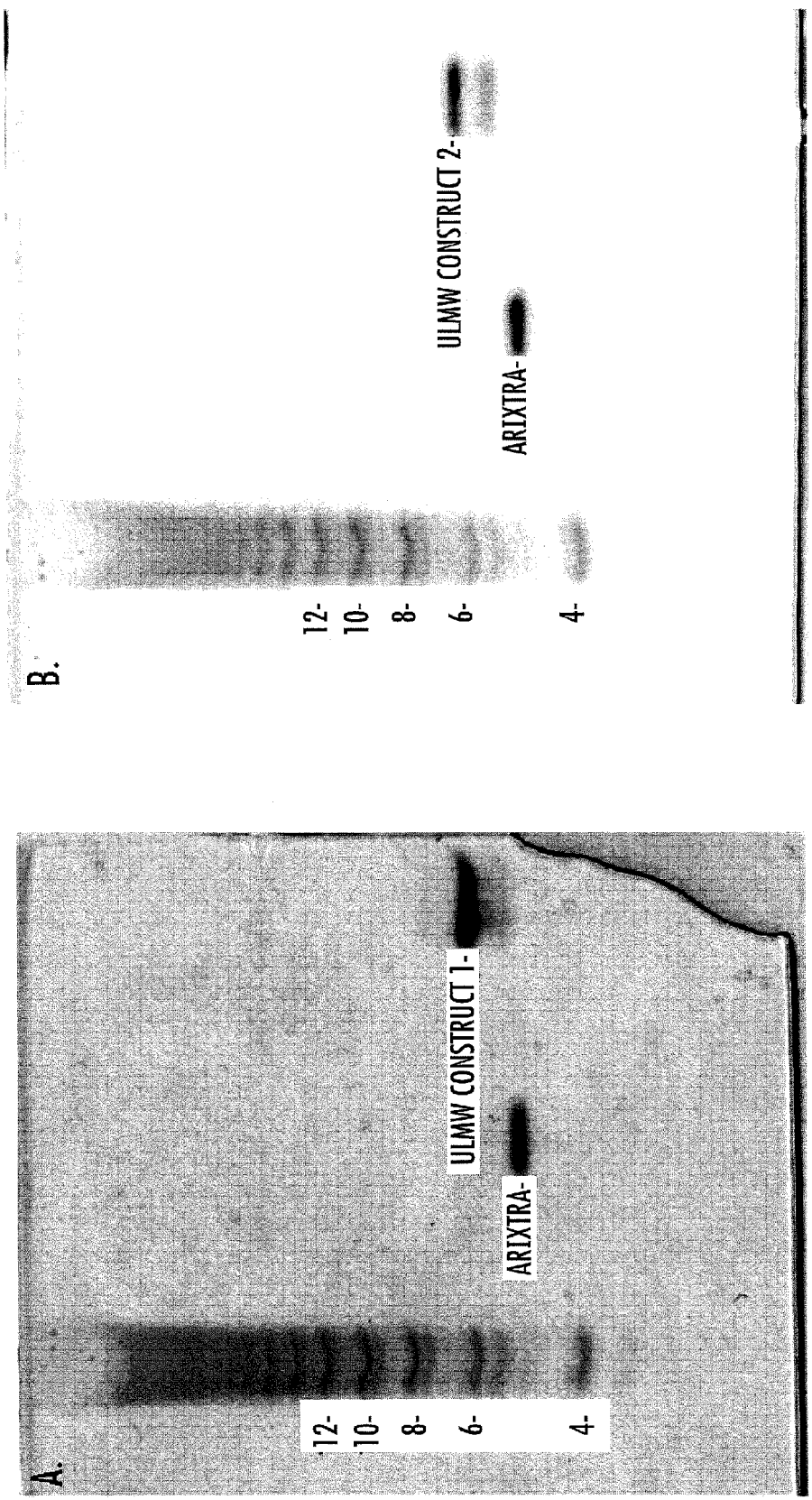

FIGS. 7A and 7B are images of two polyacrylamide gels. The gels were subject to polyacrylamide gel electrophoresis (PAGE) for the assessment of the purity of ARIXTRA® synthetic ULMW heparin pentasaccharide and ULMW heparin constructs. ULMW heparin construct 1 was analyzed on the gel shown in FIG. 7A. ULMW heparin construct 2 was analyzed on the gel shown in FIG. 7B. Results of the PAGE analysis are discussed in Example 3.

Figure 8:
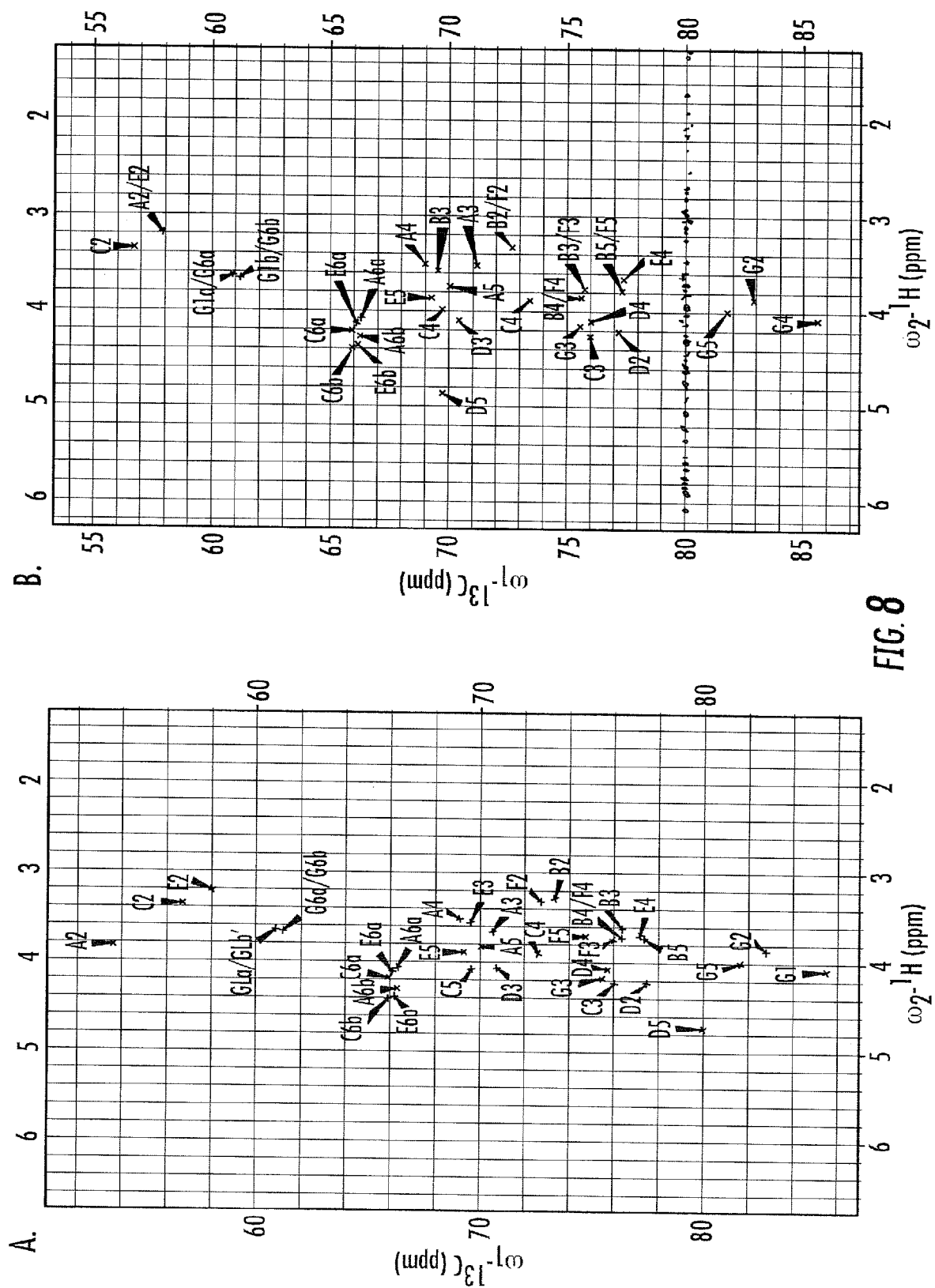

FIGS. 8A and 8B depict the results of $^1$H-$^{13}$C HMQC analysis of ULMW heparin constructs 1 and 2, respectively. FIGS. 8A and 8B show the $^1$H-$^{13}$C HMQC spectrum of ULMW heparin constructs 1 and 2, respectively (anomeric region excluded). The A2 signal of construct 2 shifted downfield in the $^{13}$C dimension compared to construct 1 due to the presence of an N-sulfo group.

Figure 9:
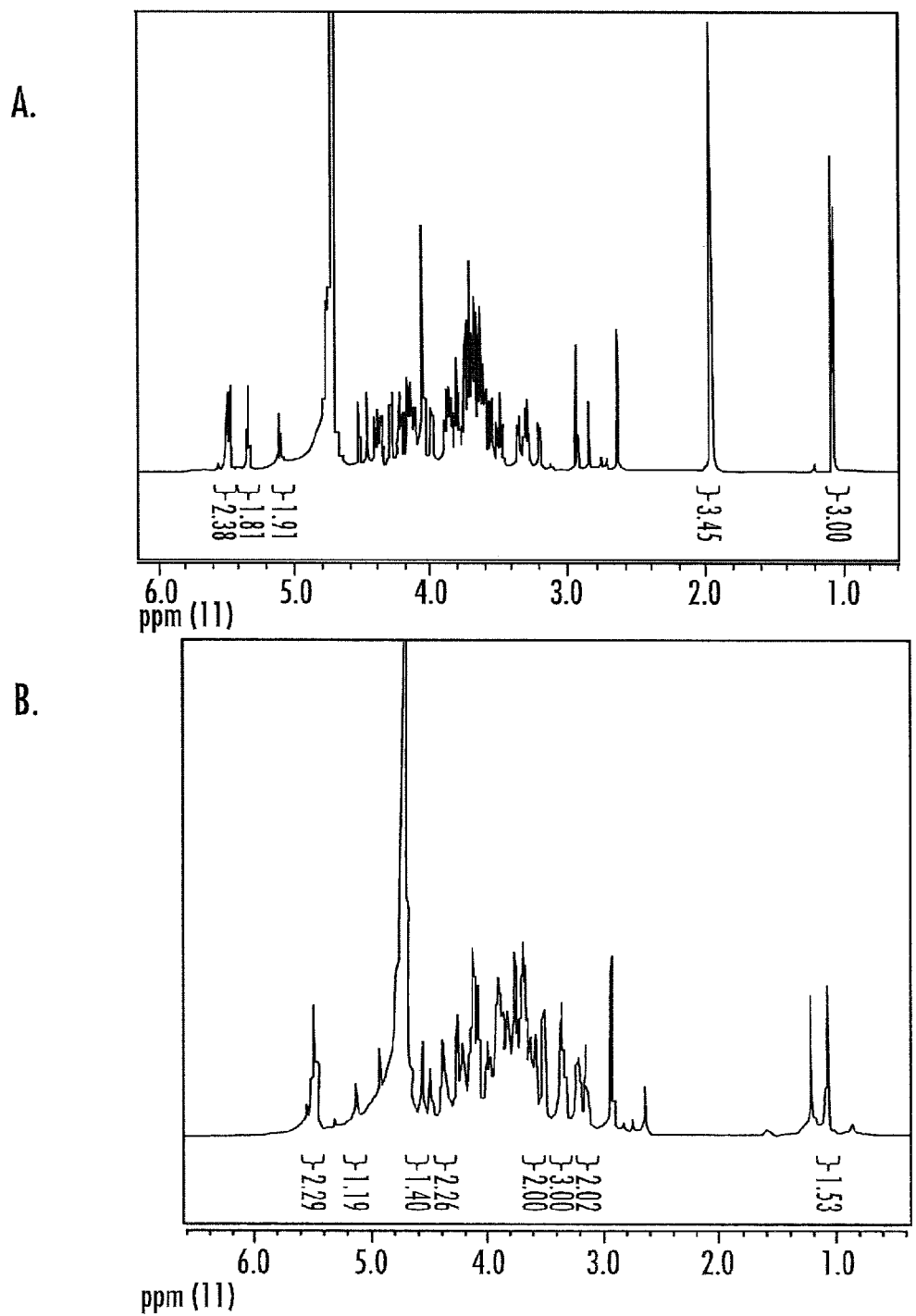

FIGS. 9A and 9B are nuclear magnetic resonance (NMR) spectroscopy spectra depicting the concentrations of ULMW heparin constructs 1 and 2 used in activity studies. The concentrations were determined as discussed in Example 4. The concentrations of constructs 1 and 2 determined by NMR were used in all of the activity studies.

FIGS. 10A and 10B are line graphs depicting the determination of the anticoagulant activities of ULMW heparin constructs 1 and 2. FIG. 10A shows the anti-Xa activity using a chromogenic substrate. In FIG. 10B, ARIXTRA® synthetic ULMW heparin pentasaccharide, construct 1 and construct 2 were each independently administered subcutaneously to rabbits and the anti-Xa activity of plasma samples was measured against a standard curve (FIG. 11). Error bars indicate the standard deviation.

FIG. 11 is a line graph of the in vitro assay method and standard curve for pharmacodynamic (PD) studies. ULMW heparin construct 1, ULMW heparin construct 2, and ARIXTRA® synthetic ULMW heparin pentasaccharide stock solutions were prepared at different concentrations, covering the range between 1 and 30 µg/mL in phosphate buffered saline, and their respective anti-Xa activities were measured.

Figure 12:
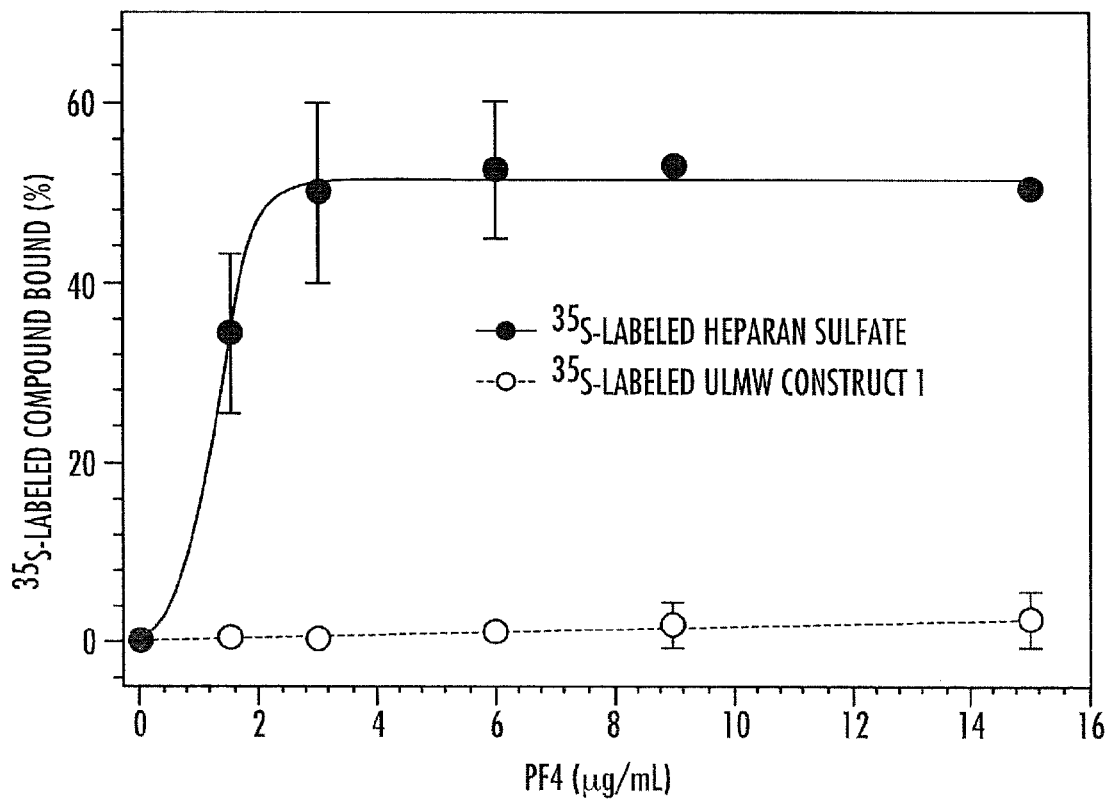

FIG. 12 is a line graph depicting the comparison of the binding of $^{35}$S-labeled heparan sulfate and $^{35}$S-labeled ULMW construct 1 to platelet factor 4 (PF4). $^{35}$S-labeled compound was incubated with various concentration of PF4. The complex of PF4 and $^{35}$S-labeled compound was captured by nitrocellulose membrane.

Figure 13:
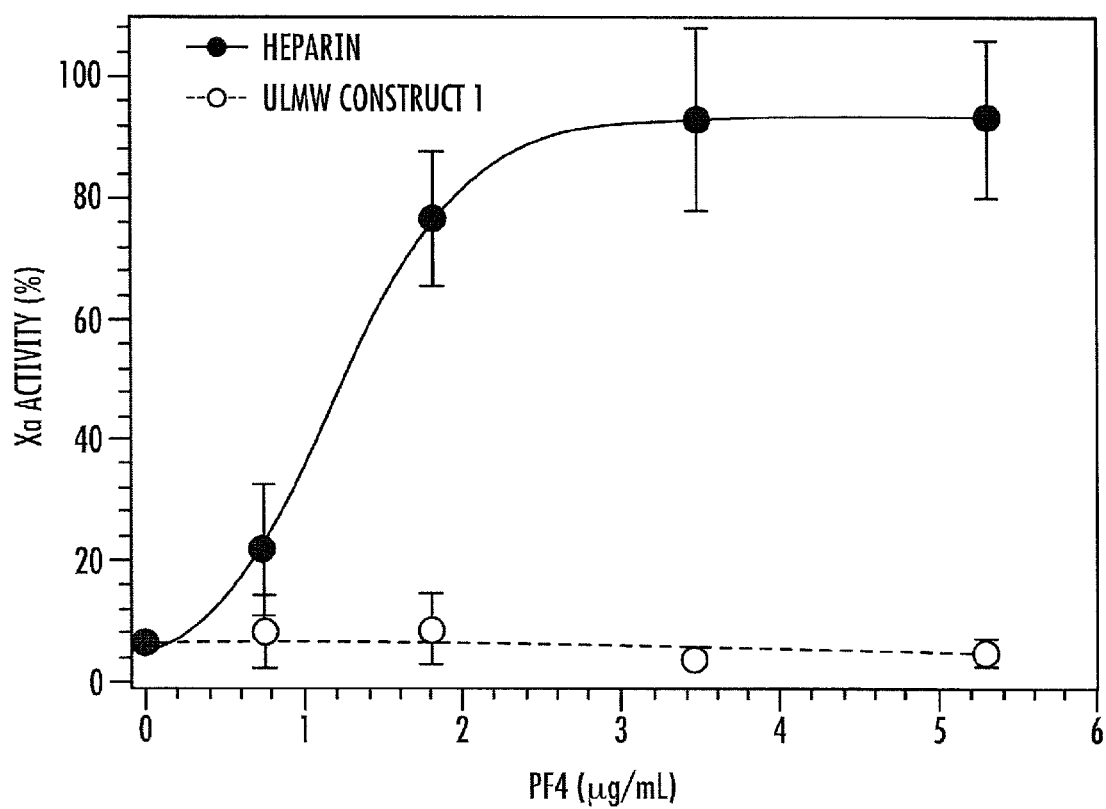

FIG. 13 is a line graph depicting the anti-Xa effect of heparin and ULMW construct 1 in the presence of PF4. Because ULMW construct 1 does not bind PF4, the anti-Xa activity of ULMW construct 1 was not affected by the presence of PF4.

DETAILED DESCRIPTION

I. Definitions

Throughout the specification and claims, a given chemical formula or name shall encompass all optical isomers and stereoisomers, as well as racemic mixtures where such isomers and mixtures exist.

Unless otherwise indicated, all numbers expressing quantities of ingredients, reaction conditions, and so forth used in the specification of the presently disclosed subject matter are to be understood as being modified in all instances by the term "about". The term "about", as used herein when referring to a measurable value such as an amount of mass, weight, time, volume, temperature, pressure, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification of the presently disclosed subject matter are approximations that can vary depending upon the desired properties sought to be obtained by the presently disclosed subject matter.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the terms "heparins", "heparin compound", "HS", "HS-like compound", and "HS-like molecule" are intended to refer to synthetically sulfated polysaccharides possessing one or more structural and/or functional properties of heparan sulfates. In some embodiments, heparin compounds can contain glucuronic acid or iduronic acid and glucosamine with or without sulfo groups. As such, heparin compounds include, but are not limited to, synthetic HSs, sulfated polysaccharides and heparins.

As used herein, the term ultra-low molecular weight (ULMW) heparin, or ULMWH, is intended to refer to a heparin compound ranging in size from 1500 to 3000 Da and having from about 5 to 10 saccharide units, and in some embodiments having anticoagulant activity. In some embodiments, a ULMW heparin of the presently disclosed subject matter can be about 1500 Da, about 1600 Da, about 1700 Da, about 1800 Da, about 1900 Da, about 2000 Da, about 2100 Da, about 2200 Da, about 2300 Da, about 2400 Da, about 2500 Da, about 2600 Da, about 2700 Da, about 2800 Da, about 2900 Da, or about 3000 Da. In some embodiments, a ULMW heparin of the presently disclosed subject matter can have 5, 6, 7, 8, 9 or 10 saccharide units. In some embodiments, a ULMW heparin of the presently disclosed subject matter can have anticoagulant activity that specifically inhibits the activity of factor Xa, without significantly inhibiting thrombin activity.

II. General Considerations

Heparan sulfates (HSs) are highly sulfated polysaccharides present on the surface of mammalian cells and in the extracellular matrix in large quantities. HS is a highly charged polysaccharide comprising 1→4-linked glucosamine and glucuronic/iduronic acid units that contain both N- and O-sulfo groups. Heparin, a specialized form of HS, is a commonly used anticoagulant drug. Thus, "heparan sulfate", as used herein, includes heparin.

Heparin compounds of the presently disclosed subject matter can comprise a synthetically sulfated polysaccharide possessing one or more structural and/or functional properties of heparan sulfates. Although exemplary embodiments of particular heparin compounds have been disclosed herein, the presently disclosed subject matter is not intended to be limited to the disclosed examples, but rather heparin compounds include all comparable synthetically sulfated polysaccharides as would be apparent to one of ordinary skill. Indeed, one of ordinary skill in the art, upon a review of the instant disclosure, is capable of producing numerous heparin compounds based upon the disclosed methods and compounds.

Heparins play roles in a variety of important biological processes, including assisting viral infection, regulating blood coagulation and embryonic development, suppressing tumor growth, and controlling the eating behavior of test subjects by interacting with specific regulatory proteins (Liu, J., and Thorp, S. C. (2002) Med. Res. Rev. 22:1-25; Rosenberg, R. D., et al., (1997) J. Clin. Invest. 99:2062-2070; Bernfield, M., et al., (1999) Annu. Rev. Biochem. 68:729-777; Alexander, C. M., et al., (2000) Nat. Genet. 25:329-332; Reizes, O., et al., (2001) Cell 106:105-116). The unique sulfated saccharide sequences can determine to which specific proteins heparins bind, thereby regulating biological processes.

The biosynthesis of heparin occurs in the Golgi apparatus. It can initially be synthesized as a copolymer of glucuronic acid and N-acetylated glucosamine by D-glucuronyl and N-acetyl-D-glucosaminyltransferase, followed by various modifications (Lindahl, U., et al., (1998) J. Biol. Chem. 273:24979-24982). These modifications can include N-deacetylation and N-sulfation of glucosamine, $C_5$ epimerization of glucuronic acid to form iduronic acid residues, 2-O-sulfation of iduronic and glucuronic acid, as well as 6-O-sulfation and 3-O-sulfation of glucosamine. Several enzymes that are responsible for the biosynthesis of HS have been cloned and characterized (Esko, J. D., and Lindahl, U. (2001) J. Clin. Invest. 108:169-173).

The expression levels of various HS biosynthetic enzyme isoforms contribute to the synthesis of specific saccharide sequences in specific tissues. HS N-deacetylase/N-sulfotransferase, 3-O-sulfotransferase, and 6-O-sulfotransferase are present in multiple isoforms. Each isoform is believed to recognize a saccharide sequence around the modification site in order to generate a specific sulfated saccharide sequence (Liu, J., et al., (1999) J. Biol. Chem. 274:5185-5192; Aikawa, J.-I., et al., (2001) J. Biol. Chem. 276:5876-5882; Habuchi, H., et al., (2000) J. Biol. Chem. 275:2859-2868). For instance, HS D-glucosaminyl 3-O-sulfotransferase (3-OST) isoforms generate 3-O-sulfated glucosamine residues that are linked to different sulfated iduronic acid residues. 3-OST isoform 1 (3-OST-1) transfers sulfate to the 3-OH position of an N-sulfated glucosamine residue that is linked to a glucuronic acid residue at the nonreducing end (GlcUA-GlcNS±6S). However, 3-OST isoform 3 (3-OST-3) transfers sulfate to the 3-OH position of an N-unsubstituted glucosamine residue that is linked to a 2-O-sulfated iduronic acid at the nonreducing end (IdoUA2S-GlcNH$_2$±6S) (Liu, J., et al., (1999) J. Biol. Chem. 274:38155-38162). The difference in the substrate specificity of 3-OSTs results in distinct biological functions. For example, the HS modified by 3-OST-1 binds to antithrombin (AT) and possesses anticoagulant activity (Liu, J., et al., (1996) J. Biol. Chem. 271:27072-27082). However, the HS modified by 3-OST-3 (3-OST-3A and 3-OST-3B) binds to glycoprotein D (gD) of herpes simplex virus, type 1, (HSV-1) thus mediating viral entry (Shukla, D., et al., (1999) Cell 99:13-22).

Cell surface HS also assists HSV-1 infection (WuDunn, D., and Spear, P. G. (1989) J. Virol. 63:52-58). One report (Shukla, D., et al., (1999) Cell 99:13-22) suggests that a specific 3-O-sulfated HS is involved in assisting HSV-1 entry. The 3-O-sulfated HS is generated by 3-OST-3 but not by 3-OST-1. In addition, the 3-O-sulfated HS provides binding sites for HSV-1 envelope glycoprotein D, which is a key viral protein involved in the entry of HSV-1 (Shukla, D., et al., (1999) Cell 99:13-22). Because 3-OST-3-modified HS is rarely found in HS from natural sources, the study suggests that HSV-1 recognizes a unique saccharide structure. Indeed, the result from the structural characterization of a gD-binding octasaccharide revealed that the octasaccharide possesses a specific saccharide sequence (Liu, J., et al., (2002) J. Biol. Chem. 277:33456-33467). In addition, the binding affinity of the 3-O-sulfated HS for gD is about 2 µM (Shukla, D., et al., Cell 99:13-22). This affinity is similar to that reported for the binding of gD to the protein receptors, suggesting that HSV-1 utilizes both protein and HS cell surface receptors to infect target cells (Willis, S. H., et al., (1998) J. Virol. 72:5938-5947; Krummenacher, C., et al., (1999) J. Virol. 73:8127-8137). It is believed that the interaction between gD and the 3-O-sulfated protein entry receptors somehow triggers the fusion between the virus and the cell in the presence of other viral envelope proteins, including gB, gH, and gL (Shukla, D., and Spear, P. G. (2001) J. Clin. Invest. 108:503-510). A study of the co-crystal structure of gD and herpes entry receptor HveA suggests that the binding of HveA to gD induces conformational changes in gD (Carfi, A., et al., (2001) Mol. Cell 8:169-179).

HS-regulated anticoagulation mechanisms have been studied extensively. It is now known that HS, including heparin, interact with AT, a serine protease inhibitor, to inhibit the activities of thrombin and factor Xa in the blood coagulation cascade (Rosenberg, R. D., et al., (1997) J. Clin. Invest. 99:2062-2070). Anticoagulant-active HS(HS$^{act}$) and heparin contain one or multiple AT-binding sites per polysaccharide chain. This binding site contains a specific pentasaccharide sequence with a structure of —GlcNS (or Ac)$_6$S-GlcUA-GlcNS3S(±6S)-IdoUA2S-GlcNS6S—. The 3-O-sulfation of glucosamine for generating GlcNS3S(±6S) residue, which is carried out by 3-OST-1, plays a role in the synthesis of HS$^{act}$ (Liu, J., et al., (1996) J. Biol. Chem. 271:27072-27082; Shworak, N. W., et al., (1997) J. Biol. Chem. 272:28008-28019).

In accordance with some embodiments, heparin compounds of the presently disclosed subject matter can have a strong binding affinity for AT. By way of non-limiting example, the binding constant ($K_d$) of heparin compounds of the presently disclosed subject matter can range from about 3 to about 100 nM. In some embodiments, the binding constant ($K_d$) of a heparin compound of the presently disclosed subject matter can range from about 3 to about 12 nM. Any suitable approach to determine binding affinity can be employed as would be appreciated by one of ordinary skill in the art upon review of the instant disclosure.

In some embodiments the anticoagulant activity can be measured by determining anti-Xa and anti-IIa activities. In some embodiments, the anti-Xa and anti-IIa activities can be determined in the presence of antithrombin.

Heparin compounds with a strong binding affinity for AT and/or a high anticoagulant activity can have high anti-Xa and anti-IIa activities. In some embodiments, heparin compounds with high anticoagulant activity can have $IC_{50}$ values for anti-Xa activity ranging from about 1 to about 20 nM. In some embodiments, heparin compounds with high anticoagulant activity can have $IC_{50}$ values for anti-Xa activity ranging from about 1 to about 5 nM. Any suitable approach to determine anticoagulant activity can be employed as would be appreciated by one of ordinary skill in the art upon review of the instant disclosure.

III. Chemoenzymatic Synthesis of Ultra-Low Molecular Weight Heparins

In some embodiments the presently disclosed subject matter provides enzymatic approaches to synthesize ultra-low molecular weight heparin compounds, including structurally homogeneous ultra-low molecular weight heparin compounds. Provided herein are two exemplary synthetic heparin oligosaccharides with anticoagulant activity. These heparin compounds are referred to herein as ULMW heparin construct 1, or simply construct 1 (also referred to as porcine-like ultra-low molecular weight heparin), and ULMW heparin construct 2, or simply construct 2 (also referred to as bovine-like ultra-low molecular heparin). The heparin compounds disclosed herein can be synthesized from a disaccharide building block using an enzymatic approach as described hereinbelow.

Figure 1A:
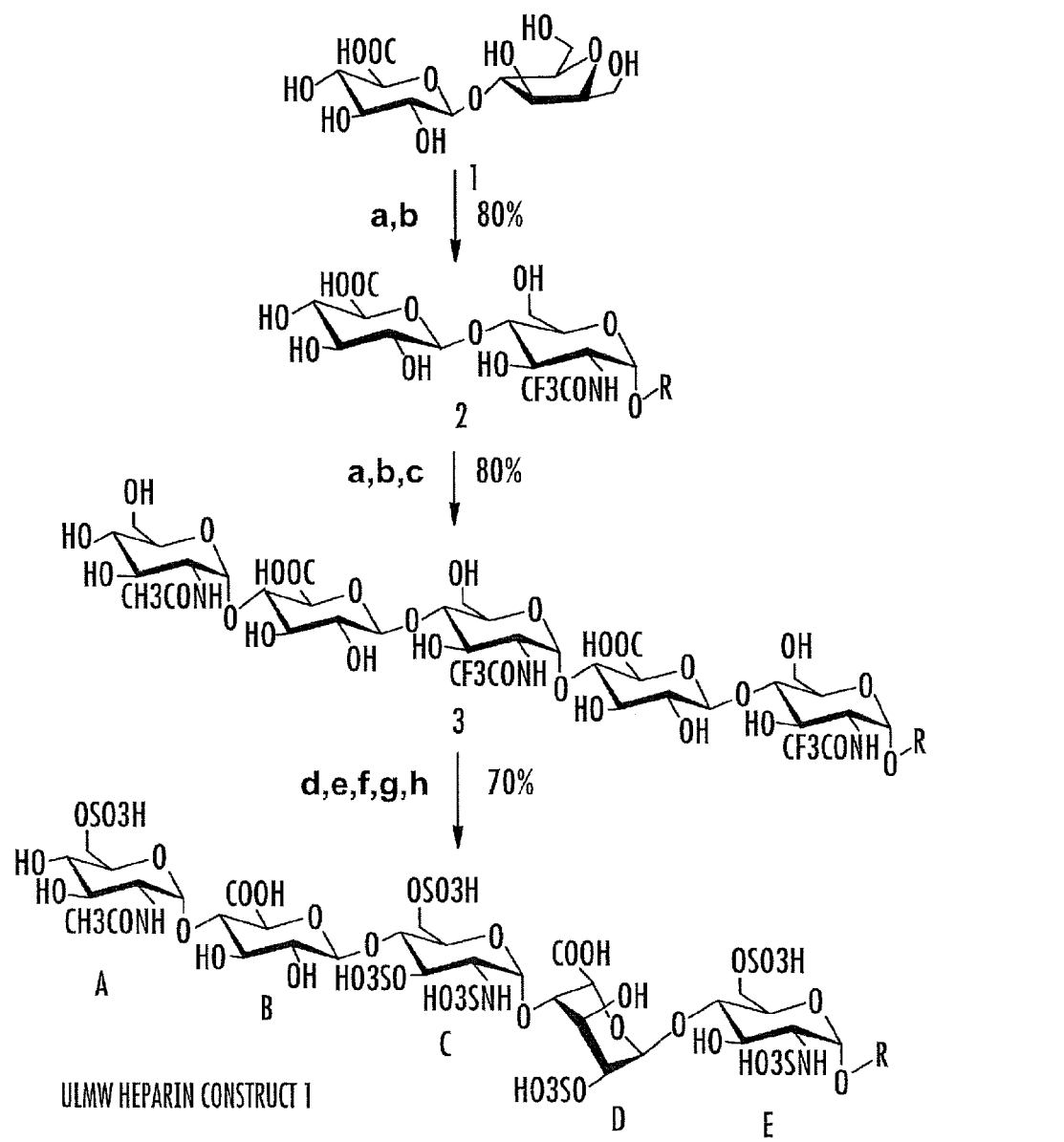
FIGS. 1A and 1B are schematic illustrations of the chemoenzymatic synthetic schemes of ultra-low molecular weight (ULMW) heparin constructs 1 and 2, respectively, of the presently disclosed subject matter.
Figure 1A:
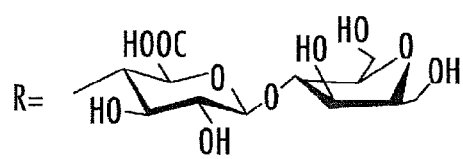
Figure 1B:
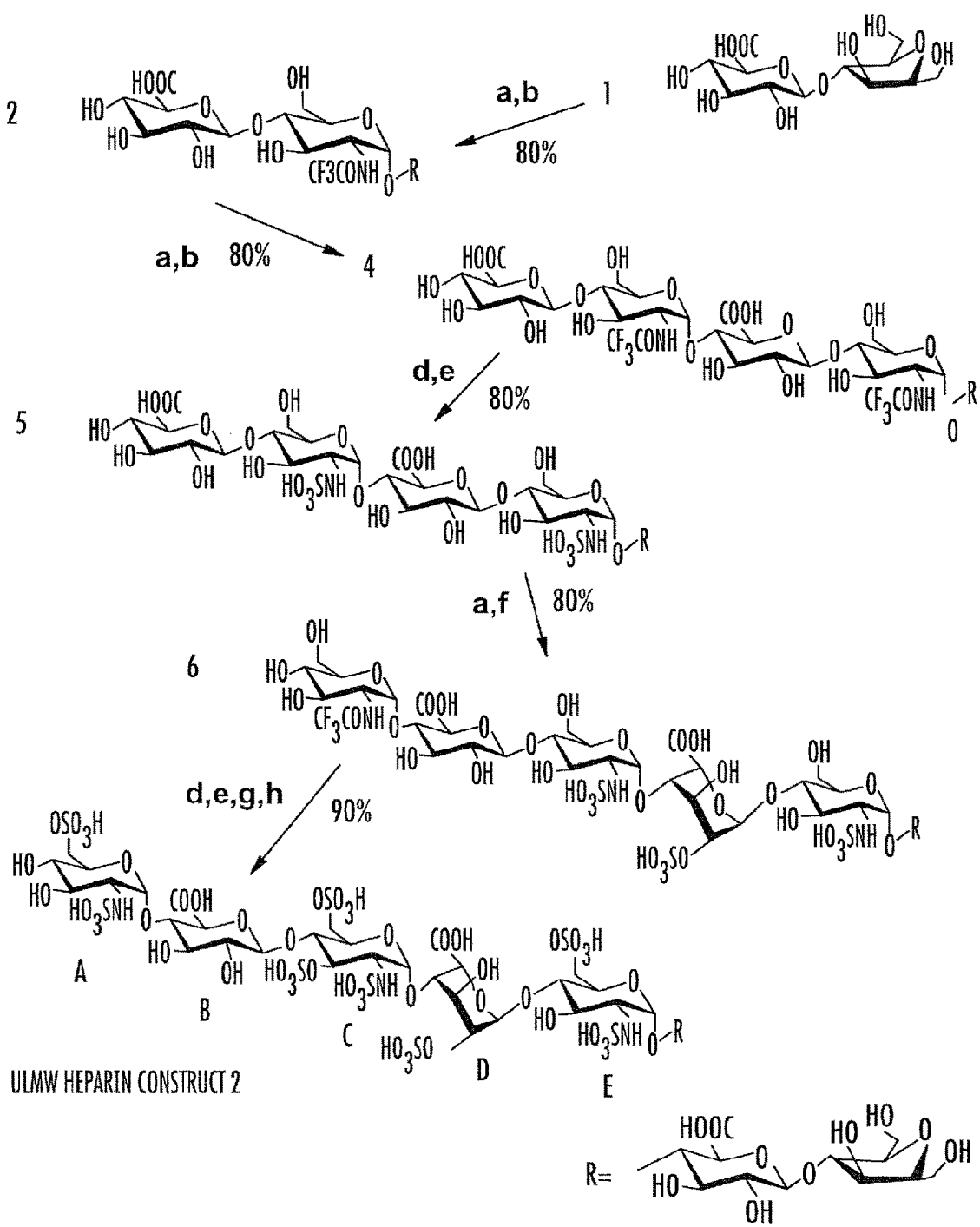

ULMW heparin constructs 1 and 2 were designed and synthesized using the disclosed chemoenzymatic approaches illustrated in FIGS. 1A and 1B. FIGS. 1A and 1B are schematic illustrations of the chemoenzymatic synthetic schemes of ULMW heparin constructs 1 and 2, respectively. FIG. 1A provides a schematic illustration of ULMW heparin construct 1. FIG. 1B provides a schematic illustration of ULMW heparin construct 2.

In some embodiments, the synthesis of ULMW heparins according to the presently disclosed subject matter can include backbone elongation and saccharide modification (FIGS. 1A and 1B). In some embodiments, the presently disclosed subject matter provides a method of synthesizing a heparin compound, comprising providing a saccharide substrate, elongating the saccharide substrate to a saccharide of a desired or predetermined length, performing an epimerization reaction, and performing one or more sulfation reactions, whereby a heparin compound is synthesized. Alternatively, in some embodiments, the presently disclosed subject matter provides a method of synthesizing a heparin compound, comprising providing a disaccharide substrate, elongating the disaccharide substrate to a tetrasaccharide, elongating the tetrasaccharide to a hexasaccharide or heptasaccharide, wherein the hexasaccharide or heptasaccharide comprises a N-sulfotransferase substrate residue, converting the N-sulfotransferase substrate residue on the hexasaccharide or heptasaccharide to a N-sulfo glucosamine (GlcNS) residue performing an epimerization reaction, and performing one or more sulfation reactions selected from the group consisting of a 2-O-sulfation reaction, a 6-O-sulfation reaction, a 3-O-sulfation reaction, and combinations thereof, whereby a heparin compound is synthesized.

In some embodiments, the elongation step can comprise employing a glycosyl transferase. By way of example and not limitation, the glycosyl transferase can be N-acetyl glucosaminyl transferase of *E. coli* K5 (KfiA) or heparosan synthase-2 (pmHS2) from *Pasteurella multocida*. In some embodiments, the elongation step can comprise employing one or more monosaccharides, which can comprise, for example, glucuronic acid (GlcUA), N-acetylated glucosamine (GlcNAc), and N-trifluoroacetyl glucosamine (GlcNTFA).

In some embodiments, the step of converting the N-sulfotransferase substrate residue on the hexasaccharide or heptasaccharide to a N-sulfo glucosamine (GlcNS) residue can comprise employing N-sulfotransferase (NST) and 3'-phosphoadenosine 5'-phosphosulfate (PAPS).

To elaborate further, in some embodiments the epimerization reaction can comprise employing $C_5$-epimerase ($C_5$-epi), the 2-O-sulfation reaction can comprise employing 2-O-sulfotransferase (2-OST), the 6-O-sulfation reaction can comprise employing 6-O-sulfotransferase (6-OST), and the 3-O-sulfation reaction can comprise employing 3-O-sulfotransferase (3-OST).

In some embodiments, a step of elongating a hexasaccharide to a heptasaccharide can comprise using a glycosyl transferase. In some aspects, the glycosyl transferase can be N-acetyl glucosaminyl transferase of *E. coli* K5 (KfiA).

In some embodiments, a ULMW heparin compound synthesized by the chemoenzymatic methods described herein can comprise the following structure:

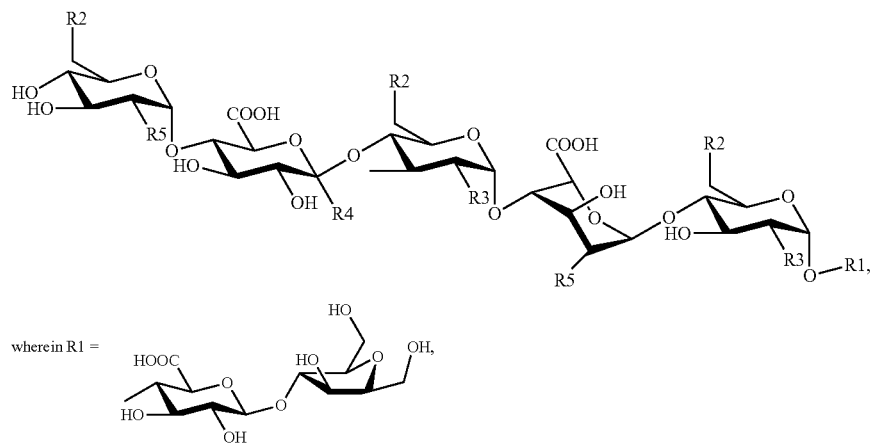

wherein R2 is OH, OSO₃H, OCH₃, or OCH₂CH₃; R3 is NHSO₃H or NHCOCH₃; R4 is OH, OSO₃H, OCH₃, or OCH₂CH₃; R5 is NHSO₃H or NHCOCH₃; and R6 is OH, OSO₃H, OCH₃, or OCH₂CH₃.

Referring to FIGS. 1A and 1B, in some embodiments the synthesis of ULMW heparin constructs 1 and 2 can start from disaccharide 1, which can then be elongated to tetrasaccharide 2. In some embodiments, eight steps (steps a, b, c, d, e, f, g and h) can be employed to prepare ULMW heparin construct 1 (FIG. 1A) from the elongated to tetrasaccharide 2. In some embodiments, steps d through h can be combined in sequential one-pot reaction format. In some embodiments, ten steps (steps a, b, d, e, a, f, d, e, g and h) can be employed to prepare ULMW heparin construct 2 (FIG. 1B) from the elongated to tetrasaccharide 2. The recovery yield at each purification step can be determined by parallel synthesis of the corresponding radioactively labeled oligosaccharide.

As depicted in FIG. 1A, in some embodiments disaccharide 1 can comprise the following structure:

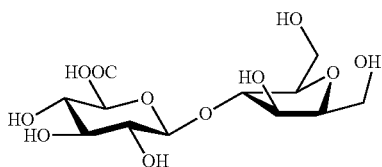

In some embodiments tetrasaccharide 2 can comprise the following structure:

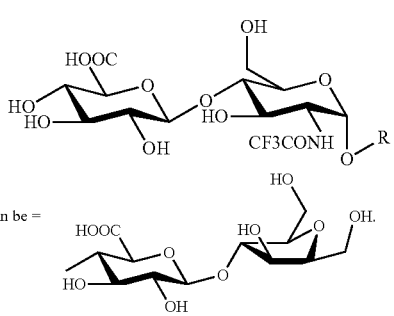

In some embodiments heptasaccharide 3 can comprise the following structure:

To elaborate, in some embodiments disaccharide 1 can be utilized as the starting material and glycosyl acceptor. In some embodiments, a disaccharide can be elongated by glycosyl transferases and prepared in multi-gram quantities from heparosan. Elongation of disaccharide 1 to tetrasaccharide 2 can be completed in some embodiments using two bacterial glycosyl transferases, N-acetyl glucosaminyl transferase of *E. coli* K5 (KfiA; Chen et al., 2006) and heparosan synthase-2 (pmHS2) from *Pasteurella multocida* (Sismey-Ragatz et al., 2007). In some embodiments, tetrasaccharide 2 can be designed with an unnatural monosaccharide, GlcNTFA (N-trifluoroacetyl glucosamine), since the N-TFA group can be readily converted to an N-sulfo group in a later step. Alternatively, in some embodiments any monosaccharide comprising a moiety that is readily converted to an N-sulfo group, as would be appreciated by one of ordinary skill in the art, can be employed without departing from the scope of the instant disclosure.

In preparing ULMW heparin construct 1, in some embodiments tetrasaccharide 2 can be elongated to heptasaccharide 3 in three steps with an overall yield of about 80% (FIG. 1A, step a, b and c). In some embodiments, heptasaccharide 3 can be converted to the final product by a series of chemoenzymatic reactions, including conversion of the GlcNTFA residue to GlcNS (FIG. 1A, steps d and e), epimerization and 2-O-sulfation (FIG. 1A, step f, here epimerization of GlcUA to IdoUA is accompanied by 2-O-sulfation using 2-OST to form an IdoUA2S at residue D), 6-O-sulfation (FIG. 1A, step g) and 3-O-sulfation (FIG. 1A, step h, the 3-O-sulfation occurred at the residue C). In approximately ten steps, the synthesis of construct 1 can be completed in this representative embodiment.

Figure 5:
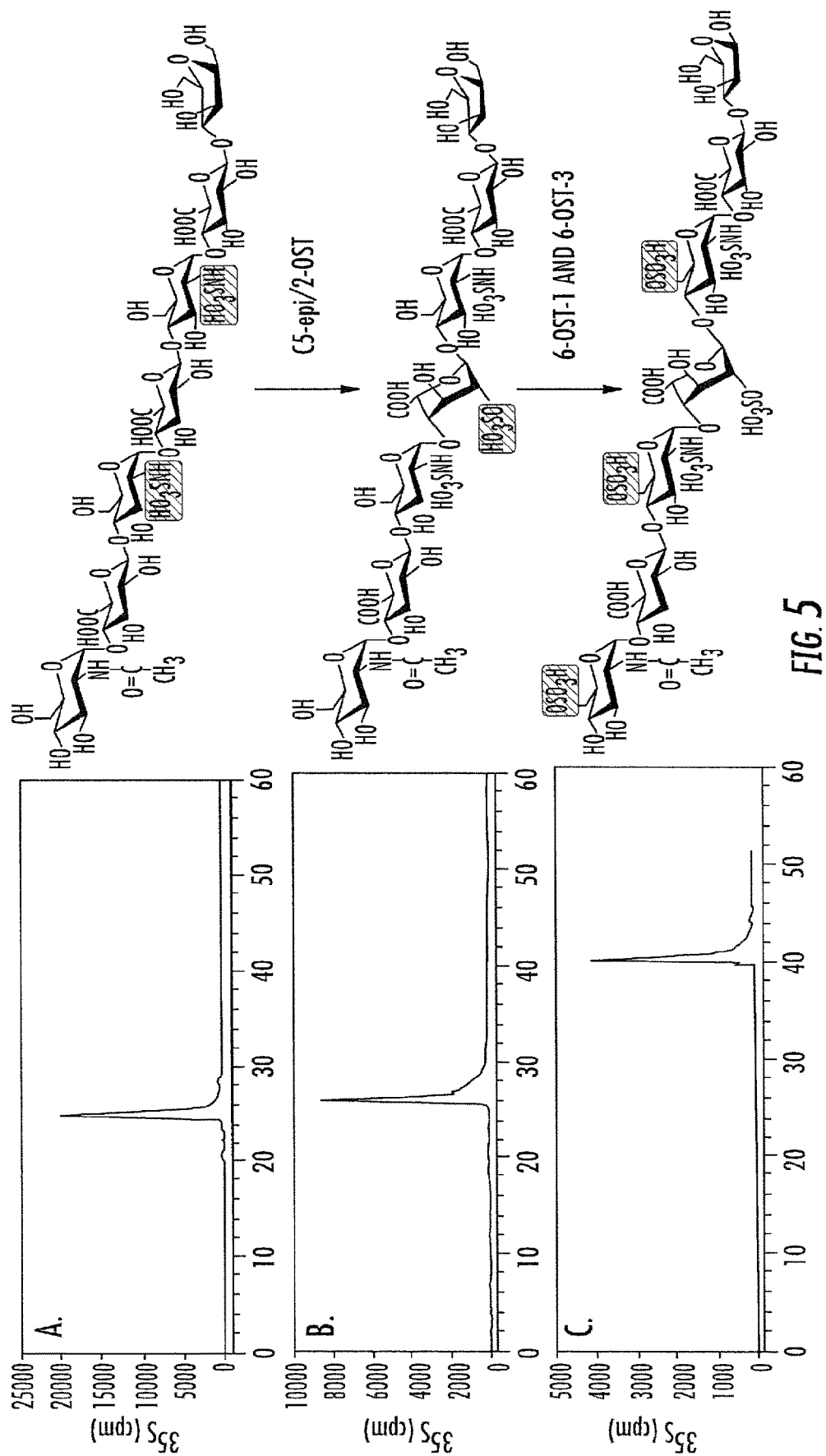
FIGS. 5A, 5B and 5C depict DEAE-HPLC chromatograms of $^{35}$S-labeled intermediates during the preparation of ULMW heparin construct 1.

In some embodiments, the conversion of heptasaccharide 3 to ULMW heparin construct 1 can be desirable to ensure that each modification was completed. For this purpose, small-scale reactions can be carried out in parallel utilizing [³⁵S]PAPS to form the ³⁵S-labeled intermediates and monitored by DEAE-HPLC, enabling the ability to anticipate the reagent concentrations and reaction times required in large-scale synthesis (FIG. 5).

3

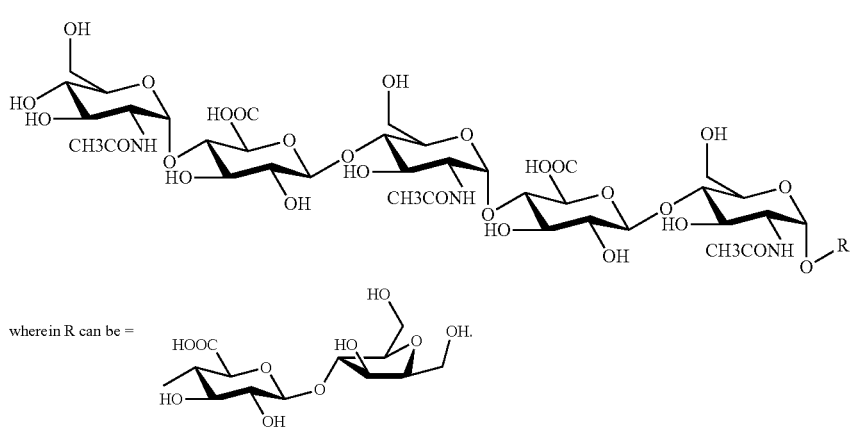

Summarily, ULMW heparin construct 1 can in some embodiments be synthesized by providing a disaccharide substrate; elongating the disaccharide substrate to a tetrasaccharide using enzymes N-acetyl glucosaminyl transferase and heparosan synthase-2, and substrates glucuronic acid (GlcUA) and N-trifluoroacetyl glucosamine (GlcNTFA); elongating the tetrasaccharide to a heptasaccharide using enzymes N-acetyl glucosaminyl transferase and heparosan synthase-2, and substrates glucuronic acid (GlcUA), N-trifluoroacetyl glucosamine (GlcNTFA), and N-acetylated glucosamine (GlcNAc); converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), triethylamine, $CH_3OH$, and $H_2O$; epimerizing the heptasaccharide using $C_5$-epimerase ($C_5$-epi); sulfating the heptasaccharide using 2-O-sulfotransferase (2-OST) and 3'-phosphoadenosine 5'-phosphosulfate (PAPS); sulfating the heptasaccharide using 6-O-sulfotransferase (6-OST) and 3'-phosphoadenosine 5'-phosphosulfate (PAPS); and sulfating the heptasaccharide using 3-O-sulfotransferase (3-OST) and 3'-phosphoadenosine 5'-phosphosulfate (PAPS).

In some embodiments, a ULMW heparin compound I produced by the above method can comprise the following structure:

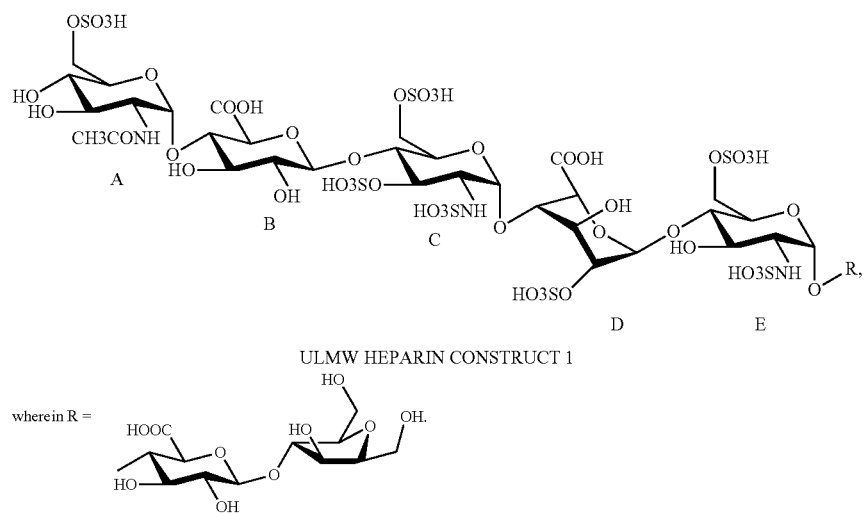

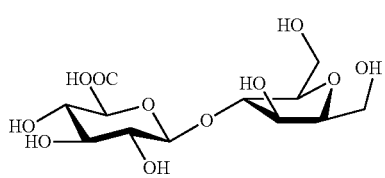

ULMW HEPARIN CONSTRUCT 1

A, B, C, D and E are used as references for the respective residues.

Referring now to ULMW heparin construct 2, and as depicted in FIG. 1B, in some embodiments disaccharide 1 can comprise the following structure:

In some embodiments tetrasaccharide 2 can comprise the following structure:

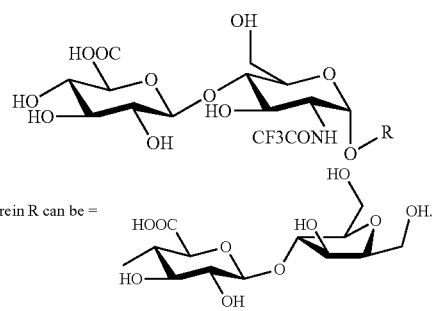

wherein R can be =

In some embodiments hexasaccharide 4 can comprise the following structure:

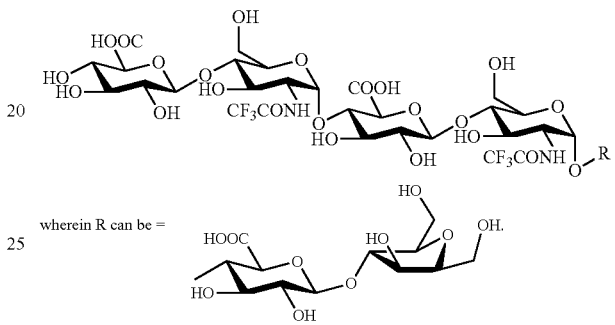

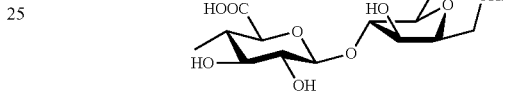

wherein R can be =

In some embodiments hexasaccharide 5 can comprise the following structure:

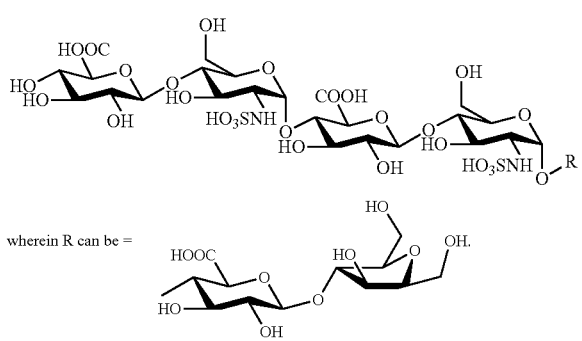

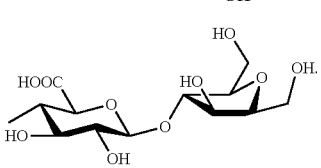

wherein R can be =

In some embodiments heptasaccharide 6 can comprise the following structure:

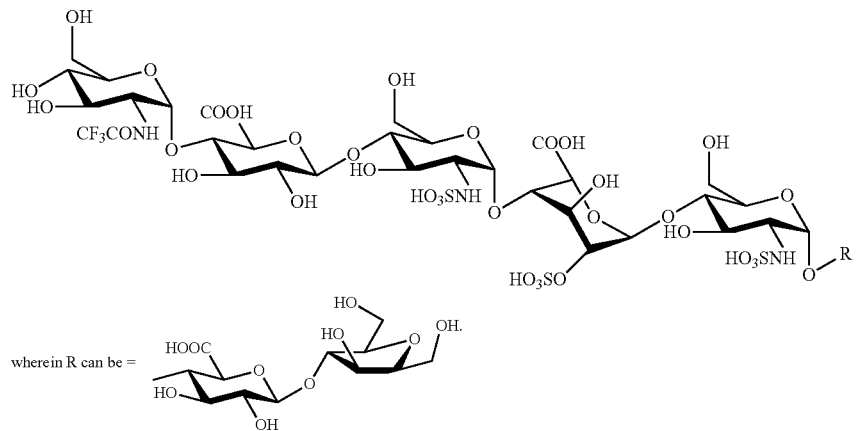

Figure 6:
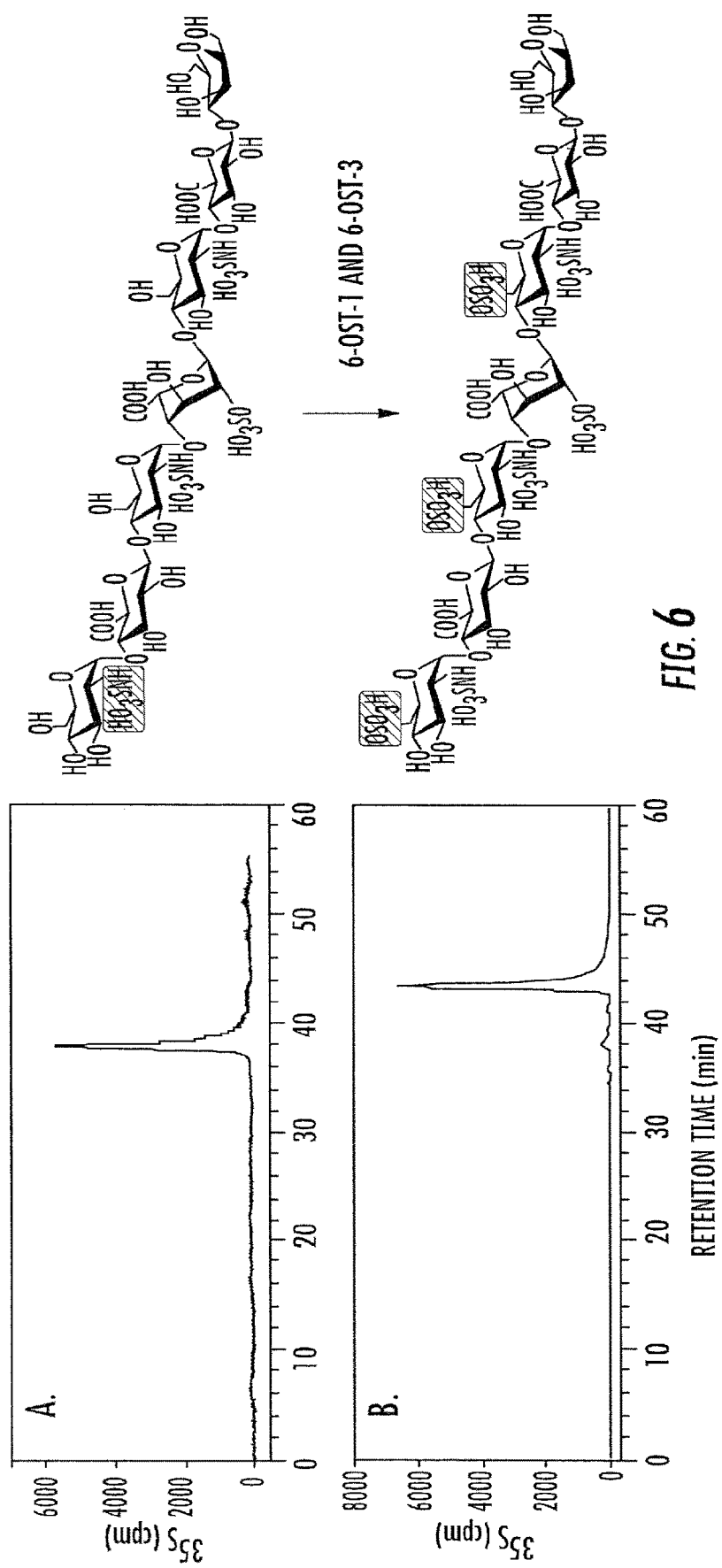

In preparing ULMW heparin construct 2, in some embodiments two extra steps can be used to add a GlcNS6S residue to the non-reducing end. Tetrasaccharide 2 can first be converted to hexasaccharide 4 (heptasaccharide 3 is included in FIG. 1A, thus no polysaccharide 3 is included in FIG. 1B to avoid confusion), and the N-TFA groups can be replaced by N-sulfo groups to afford hexasaccharide 5 (FIG. 1B). Hexasaccharide 5 can be elongated to a heptasaccharide with a non-reducing end GlcNTFA (residue A). This heptasaccharide can be treated by $C_5$-epi and 2-OST (FIG. 1B, step f) to place an IdoUA2S at residue D forming heptasaccharide 6. The introduction of a GlcNTFA residue at the non-reducing end can be a control point in this synthesis as it can prevent the action of $C_5$-epi and 2-OST on the GlcUA, (residue B in step f). Heptasaccharide 6 can then be converted to ULMW heparin construct 2 in a sequential one-pot reaction format (FIG. 1B, step d, e, g, h). Ensuring that 6-O-sulfation completed can be confirmed by carrying out a small scale reaction using [$^{35}$S]PAPS (FIG. 6).

Summarily, ULMW heparin construct 2 can in some embodiments be synthesized by providing a disaccharide substrate; elongating the disaccharide substrate to a tetrasaccharide using enzymes N-acetyl glucosaminyl transferase and heparosan synthase-2, and substrates glucuronic acid (GlcUA) and N-trifluoroacetyl glucosamine (GlcNTFA); elongating the tetrasaccharide to a hexasaccharide using enzymes N-acetyl glucosaminyl transferase and heparosan synthase-2, and substrates glucuronic acid (GlcUA) and N-trifluoroacetyl glucosamine (GlcNTFA); converting N-trifluoroacetyl glucosamine (GlcNTFA) residue(s) on the hexasaccharide to N-sulfo glucosamine (GlcNS) residues using N-sulfotransferase (NST), 3'-phosphoadenosine 5'-phosphosulfate (PAPS), triethylamine, $CH_3OH$, and $H_2O$; elongating the hexasaccharide to a heptasaccharide using enzyme N-acetyl glucosaminyl transferase and substrate N-trifluoroacetyl glucosamine (GlcNTFA); epimerizing the heptasaccharide using $C_5$-epimerase ($C_5$-epi); sulfating the heptasaccharide using 2-O-sulfotransferase (2-OST) and 3'-phosphoadenosine 5'-phosphosulfate (PAPS); converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), triethylamine, $CH_3OH$, and $H_2O$; sulfating the heptasaccharide using 6-O-sulfotransferase (6-OST) and 3'-phosphoadenosine 5'-phosphosulfate (PAPS); and sulfating the heptasaccharide using 3-O-sulfotransferase (3-OST) and 3'-phosphoadenosine 5'-phosphosulfate (PAPS).

In some embodiments, a ULMW heparin construct 2 produced by the above method can comprise the following structure:

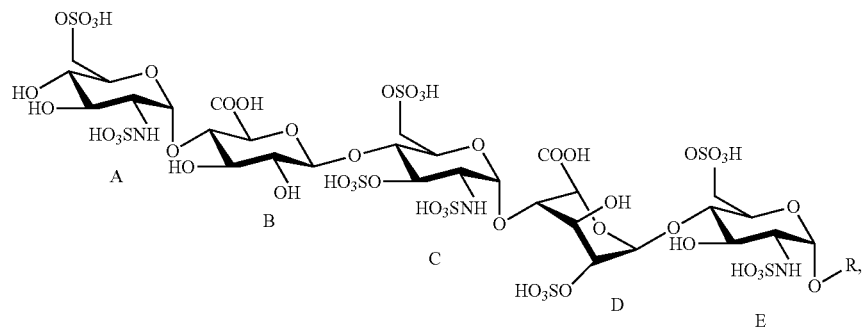

ULMW HEPARIN CONSTRUCT 2

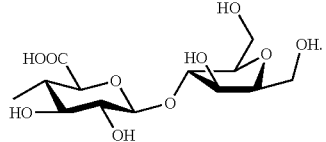

In some embodiments, a ULMW heparin construct of the presently disclosed subject matter can have an R group as indicated above, and in FIGS. 1A and 1B, wherein

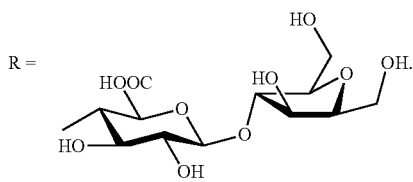

A variety of starting materials can be used in the presently disclosed methods of synthesizing ULMW heparins. By way of example and not limitation, in some embodiments a cost effective glucuronic acid derivative, i.e. the R group as depicted in FIGS. 1A and 1B, can be used for the synthesis of ULMW heparin compounds. As would be appreciated by one of ordinary skill in the art, the starting materials used for the synthesis of ULMW heparin compounds can be selected based on cost, availability, ease of making, ease of use, stability, and any other factor that might be considered in deciding which starting material is most appropriate. By way of example and not limitation, in some embodiments, the R group of a ULMW heparin compound synthesized by the presently disclosed methods can be selected from the group comprising:

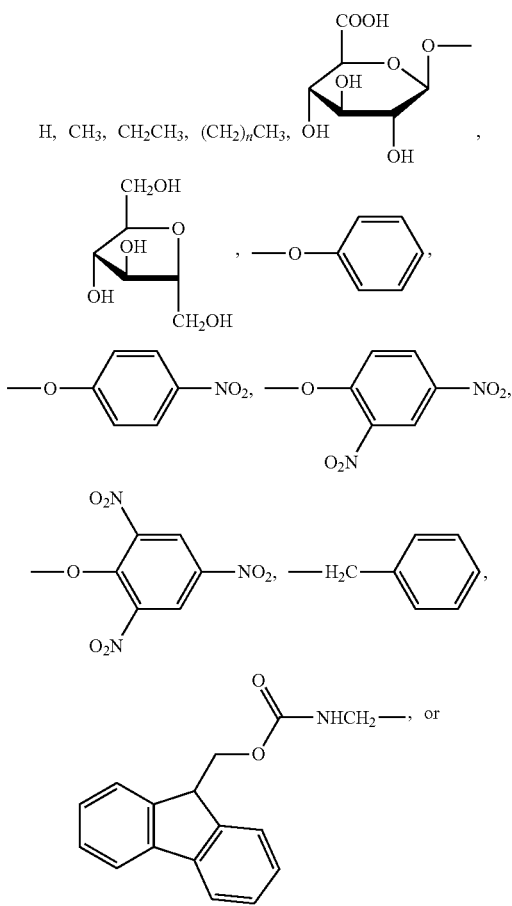

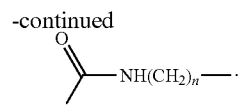

-continued

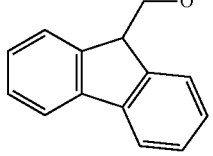

In some embodiments, a ULMW heparin construct of the presently disclosed subject matter can have an R group that has UV or visible light absorbance. Designing and synthesizing a ULMW heparin construct that has an R group that absorbs UV or visible light can facilitate product purity detection and isolation. Constructing a ULMW heparin, such as ULMW construct 1 or 2, with a UV or visible light "tag" can facilitate the monitoring of the chemoenzymatic reactions and construct synthesis. As would be appreciated by one of ordinary skill in the art, detecting a UV or visible light "tag" on a construct during or after synthesis can be achieved using any number of available spectrophotometric devices.

Alternatively, or in addition, in some embodiments the R group can be a hydrophobic R group. As would be appreciated by one of ordinary skill in the art, a hydrophobic R group can allow the product to bind to a C18-column, which can allow for the purification of the synthesized ULMW heparins.

In some embodiments, an R group, such as an R group that has UV or visible light absorbance, or a hydrophobic R group, can be removable when the synthesis of the ULMW heparin is completed. As would be appreciated by one of ordinary skill in the art, removing the R group once its utility is achieved can facilitate the final processing of the ULMW heparin construct. For example, in some aspect it might be desirable to remove the R group to avoid potential toxic functional groups entering into a ULMW heparin drug compound.

In some embodiments, a ULMW heparin compound produced by the methods disclosed herein, such as for example ULMW heparin construct 1 or 2, can have a molecular weight ranging from about 1500 to 3000 daltons (Da). In some embodiments, a ULMW heparin compound produced by the methods disclosed herein, such as for example ULMW heparin construct 1 or 2, can have anticoagulant activity. In some embodiments, such ULMW constructs can have a binding affinity to antithrombin ranging from about 3 to about 12 nM. In some embodiments, ULMW constructs can have a binding affinity to antithrombin of about 3 nM, about 4 nM, about 5 nM, about 6 nM, about 7 nM, about 8 nM, about 9 nM, about 10 nM, about 11 nM or about 12 nM. In some embodiments, ULMW constructs synthesized by the disclosed methods can have an anti-Xa activity ranging from about 1 to about 5 nM $IC_{50}$. In some embodiments, ULMW constructs can have an anti-Xa activity ranging of about 1 nM $IC_{50}$, about 2 nM $IC_{50}$, about 3 nM $IC_{50}$, about 4 nM $IC_{50}$, or about 5 nM $IC_{50}$.

In some embodiments, a ULMW heparin compound produced by the methods disclosed herein can maintain its anti-Xa activity even in the presence of platelet factor 4 (PF4). Stated another way, a ULMW heparin compound produced by the methods disclosed herein does not bind PF4. In contrast, heparin and low molecular weight heparin bind PF4, which can promote heparin-induced thrombocytopenia, a major side effect associated with using heparin. Because ULMW heparin constructs synthesized by the presently disclosed methods, e.g. constructs 1 and 2, do not bind PF4, they do not promote the heparin-induced thrombocytopenia side effect. See, e.g., FIGS. 12 and 13.

Compared to the chemical synthesis of a similar compound, the presently disclosed chemoenzymatic synthesis methods shorten the synthesis from more than 50 steps to about 10 steps. The overall yield using the presently disclosed methods has been increased from 0.1%, experienced with chemical synthesis methods, to about 40% or more. In some embodiments, the overall yield of the synthesis methods of the presently disclosed subject matter can be about 10% or more, about 20% or more, about 30% or more, about 40% or more or about 50% or more.

The heparin compounds synthesized in some embodiments are structurally homogeneous molecules, thereby affording quality control. Both representative oligosaccharides (construct 1 and construct 2) have been obtained in 5-10 mg scales. Not only is the synthesis significantly shorter as compared to chemical synthesis, in some embodiments the chemoenzymatic syntheses of the presently disclosed subject matter do not involve inorganic chemicals (i.e. it is green chemistry) and can reduce the cost of synthesizing heparin compounds.

Ultra-low molecular weight heparin includes anticoagulant heparin oligosaccharides that specifically inhibit the activity of factor Xa, without significantly inhibiting thrombin activity. ULMW heparins range from 1500 to 3000 Da, corresponding to from 5 to 10 saccharide units. In some embodiments, the presently disclosed subject matter provides for the synthesis of heparin compounds of a predetermined or desired length. A "predetermined or desired length" can comprise any number of saccharide units necessary to achieve a desired result, e.g. 5 to 10 saccharide units to achieve a ULMW heparin.

ARIXTRA® (fondaparinux sodium; GlaxoSmithKline, plc, Middlesex, United Kingdom), is a structurally homogeneous, ULMW heparin pentasaccharide that is synthesized through a lengthy chemical process (Petitou and Boeckel, 2004). The presently disclosed subject matter provides for the multi-milligram chemoenzymatic synthesis of two novel, structurally homogenous, ULMW heparins (construct 1, MW=1778.5 Da, and construct 2, MW=1816.5 Da,) with a 45% and 37% overall yield, respectively. The disclosed chemoenzymatic approach is nearly 400-fold more efficient than the chemical synthesis of ARIXTRA® synthetic ULMW heparin pentasaccharide, affording ULMW heparin constructs that display excellent activities while substantially improving the preparation of heparin-based therapeutics. Indeed, in some embodiments the presently disclosed chemoenzymatic methods can be used to synthesize an ARIXTRA® synthetic ULMW heparin pentasaccharide.

Heparin includes a disaccharide-repeating unit of either iduronic acid (IdoUA) or glucuronic acid (GlcUA) and glucosamine (GlcN) residues, each capable of carrying sulfo groups. The number and location of these sulfo groups and the positioning of IdoUA residues within oligosaccharide domains, such as the antithrombin (AT)-binding site pentasaccharide, play a role in heparin's biological functions. The chemical synthesis of the pentasaccharide ARIXTRA®, containing an AT-binding site, is one example to date for preparing an anticoagulant oligosaccharide (Petitou & Boeckel, 2004). The synthesis of ARIXTRA® pentasaccharide, however, involves approximately 50 steps and overall yield of about 0.1% (Petitou et al., 1989). Efforts for improving a purely chemical approach for the synthesis of ARIXTRA® pentasaccharide and larger oligosaccharides have shown only limited success (Noti & Seeberger, 2005).

The presently disclosed subject matter provides a chemoenzymatic approach, relying on a series of specialized enzymes, that mimics the biosynthesis of heparin and its analog, heparan sulfate (HS) (Chen et al., 2005). HS polymerases synthesize the backbone with a disaccharide repeating unit of GlcUA and N-acetylated glucosamine (GlcNAc). Subsequent modification relies on Golgi enzymes including, N-deacetylase/N-sulfotransferase (containing separate N-deacetylase and N-sulfotransferase (NST) domains), $C_5$-epimerase ($C_5$-epi), 2-O-sulfotransferase (2-OST), 6-O-sulfotransferase (6-OST) and 3-O-sulfotransferase (3-OST). The specificities of these enzymes enable the introduction of sulfo groups and to position IdoUA residues with high precision without the use of complicated protection/deprotection steps, providing a new strategy for the synthesis the oligosaccharides by much shorter routes.

Constructs 1 and 2 contain the AT-binding domains of porcine intestinal and bovine lung heparin, respectively (Loganathan et al., 1990). ULMW heparin construct 2 has the same structure as ARIXTRA® synthetic ULMW heparin pentasaccharide except for the replacement of its methyl aglycone with disaccharide 1 (FIG. 1B). This structural similarity permits the direct comparison of synthetic efficiency and the in vitro and in vivo biological activities of these two homogenous ULMW heparins to ARIXTRA® synthetic ULMW heparin pentasaccharide.

Heparin is known to display a wide range of biological activities. The diverse biological functions present opportunities for exploiting heparin or heparin-protein conjugates for developing new classes of anticancer and antiviral drugs. The presently disclosed subject matter provides methods to cost-effectively synthesize structurally defined, homogenous heparin oligosaccharides, which can be useful to improve the selectivity of heparin-based drugs. Heparin oligosaccharides are generally perceived by those of ordinary skill in the art to be too difficult to chemically synthesize due to: the long synthetic route, required by the introduction and removal of protecting groups; the low overall yield; and a lack of efficient methods to purify side-products from intermediates and products. The enzymatic approach disclosed herein shows that heparin oligosaccharides can be synthesized in a relatively small number of steps in high purity and with very high efficiency. This was achieved by using recombinant enzymes at a scale comparable to chemical synthesis. The recovery yield from enzymatic synthesis is nearly 400-fold higher than that of chemical synthesis, and the entire synthesis was completed in three to four weeks. These methods can prove useful in meeting the increased demand for a new source of selective and synthetic heparin drugs with expanded therapeutic applications. The presently disclosed methods can provide a generic and cost-effective approach for the preparation of structurally diverse heparins and heparin oligosaccharides for biological and therapeutic evaluation.

III.A. Enzymes Employed in Chemoenzymatic Synthesis of ULMW Heparins

In some embodiments, the presently disclosed subject matter can utilize sulfotransferases, epimerases, glycosyltransferases, and/or heprosan synthases, among other enzymes as would be appreciated by one of ordinary skill in the art. These enzymes, and others that would be employed by one of ordinary skill in the art, are referred to herein as "the enzymes", "these enzymes", and/or "enzymes". In some embodiments the chemoenzymatic syntheses can employ NST, $C_5$-epimerase ($C_5$-epi), 2-OST, 6-OST-1,6-OST-3,3-OST-1, N-acetyl glucosaminyl transferase of *E. coli* K5 (KfiA), and/or heparosan synthase-2 (pmHS2). In some embodiments these and other enzymes employed in the chemoenzymatic syntheses can be expressed in *E. coli* and purified by appropriate affinity chromatography as described previously (Liu et al., 2010).

In some embodiments, the chemoenzymatic syntheses employ sulfotransferases, such as O-sulfotransferases (OSTs), to sulfate polysaccharides. Sulfotransferases comprise a family of enzymes that catalyze the transfer of a sulfonate or sulfuryl group ($SO_3$) from a sulfo donor compound, i.e. an $SO_3$-donor molecule, to an acceptor molecule. By way of non-limiting example, the sulfo donor compound or $SO_3$-donor molecule can be the cofactor 3'-phosphoadenosine-5'-phosphosulfate (PAPS). Even though it is more accurate to call these sulfonation reactions, the term sulfation is still widely used. Therefore, the term "sulfation" as used herein refers to a transfer of a sulfonate or sulfuryl group from one molecule to another.

Sulfotransferases mediate sulfation of different classes of substrates such as carbohydrates, oligosaccharides, peptides, proteins, flavonoids, and steroids for a variety of biological functions including signaling and modulation of receptor binding (Bowman et al., (1999) Chem. Biol. 6, R9-R22; and Falany (1997) *FASEB J.* 11, 1-2). Many new sulfotransferases have been identified and cloned (Aikawa et al., (1999) J. Biol. Chem. 274, 2690; Dooley (1998) *Chemico-Biol. Interact.* 109, 29; Fukuta et al. (1998) *Biochim. Biophys. Act.* 1399, 57; Habuchi et al., (1998) *J. Biol. Chem.* 273, 9208; Mazany et al., (1998) *Biochim. Biophys. Act.* 1407, 92; Nastuk et al. (1998) *J. Neuroscience* 18, 7167; Ong et al., (1998) *J. Biol. Chem.* 273, 5190; Ouyang et al., (1998) *J. Biol. Chem.* 273, 24770; Saeki et al. (1998) *J. Biochem.* 124, 55; Uchimura et al. (1998) *J. Biol. Chem.* 273, 22577; and Yoshinari et al., (1998) *J. Biochem.* 123, 740).

As used herein, the term "O-sulfotransferase (OST)" includes polypeptides and nucleic acids encoding HS O-sulfotransferases, such as for example "2-OST" (e.g., mouse 2-OST, GENBANK® Accession No. AAC40135; "3-OST-1" (e.g., human 3-OST-1, GENBANK® Accession No. NP_005105; "3-OST-3" (e.g., human 3-OST-3A, GENBANK® Accession No. NP_006033 and human 3-OST-3B, GENBANK® Accession No. NP_006032; and "6-OST" (e.g., mouse 6-OST-1, GENBANK® Accession No. NP_056633, mouse 6-OST-2, GENBANK® Accession No. BAA89247, and mouse 6-OST-3, GENBANK® Accession No. NP_056635), which are HS 2-O-sulfotransferase, HS 3-O-sulfotransferase isoform 1, HS 3-O-sulfotransferase isoform 3, and HS 6-O-sulfotransferase, respectively.

The term "OST" includes invertebrate and vertebrate homologs of the O-sulfotransferases (e.g., mammalian (such as human and mouse), insect, and avian homologs). As such, although exemplary embodiments of particular OSTs have been disclosed herein, the presently disclosed subject matter is not intended to be limited to the disclosed examples, but rather "OST", including particular OSTs (e.g., 2-OST, 3-OST-1,3-OST-3, and 6-OST), includes all comparable OSTs known to the skilled artisan.

In some embodiments the disclosed chemoenzymatic syntheses can employ $C_5$-epimerase ($C_5$-epi). As such, although exemplary embodiments of particular epimerases have been disclosed herein, the presently disclosed subject matter is not intended to be limited to the disclosed examples, but rather "epimerase", including $C_5$-epi, includes all comparable epimerases known to the skilled artisan. Indeed, other epimerases, or compounds having epimerase activity, can be employed without departing from the scope of the presently disclosed subject matter.

In some embodiments the disclosed chemoenzymatic syntheses can employ N-acetyl glucosaminyl transferase of *E. coli* K5 (KfiA). As such, although exemplary embodiments of particular glucosaminyl transferase have been disclosed herein, the presently disclosed subject matter is not intended to be limited to the disclosed examples, but rather "glucosaminyl transferase", including KfiA, includes all comparable glucosaminyl transferases known to the skilled artisan. Indeed, other glucosaminyl transferases, or compounds having similar transferase activity, can be employed without departing from the scope of the presently disclosed subject matter.

In some embodiments the disclosed chemoenzymatic syntheses can employ heparosan synthase-2 (pmHS2). As such, although exemplary embodiments of particular heparosan synthases have been disclosed herein, the presently disclosed subject matter is not intended to be limited to the disclosed examples, but rather "heparosan synthase", including pmHS2, includes all comparable heparosan synthases known to the skilled artisan. Indeed, other heparosan synthases, or compounds having similar synthase activity, can be employed without departing from the scope of the presently disclosed subject matter.

The terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" refer to peptides having amino acid sequences which are substantially identical to native amino acid sequences from the organism of interest and which are biologically active in that they comprise all or a part of the amino acid sequence of an O-sulfotransferase, epimerase, glucosaminyl transferase, or heprosan synthase, or cross-react with antibodies raised against such enzymes, or retain all or some of the biological activity of the native amino acid sequence or protein of such enzymes. Such biological activity can include immunogenicity.

The terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" also include analogs of the enzymes. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct analogs of these enzymes. There is no need for a "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" to comprise all or substantially all of the amino acid sequence of a native enzyme gene product. Shorter or longer sequences are anticipated to be of use in the presently disclosed subject matter, shorter sequences are herein referred to as "segments." Thus, the terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" also include fusion or recombinant polypeptides and proteins comprising sequences of the enzyme protein. Methods of preparing such proteins are known in the art.

The terms "OST gene product", "OST protein", "OST polypeptide", "epimerase gene product", "epimerase protein", "epimerase polypeptide", "glucosaminyl transferase gene product", "glucosaminyl transferase protein", "glucosaminyl transferase polypeptide", "heparosan synthase gene product", "heparosan synthase protein", and "heparosan synthase polypeptide" refer to any DNA sequence that is substantially identical to a polynucleotide sequence encoding an enzyme isoform gene product, protein or polypeptide as defined above, and can also comprise any combination of associated control sequences. The terms also refer to RNA, or antisense sequences, complementary to such DNA sequences. As used herein, the term "DNA segment" refers to a DNA molecule that has been isolated free of total genomic DNA of a particular species. Furthermore, a DNA segment encoding a polypeptide of one of these enzymes refers to a DNA segment that contains coding sequences for one of these enzymes, yet is isolated away from, or purified free from, total genomic DNA of a source species, such as for example Homo sapiens. Included within the term "DNA segment" are DNA segments and smaller fragments of such segments, and also recombinant vectors, including, for example, plasmids, cosmids, phages, viruses, and the like.

The term "substantially identical", when used to define either a gene product of one of these enzymes or amino acid sequence, or an enzyme gene or nucleic acid sequence, means that a particular sequence varies from the sequence of a natural enzyme by one or more deletions, substitutions, or additions, the net effect of which is to retain at least some of biological activity of the natural gene, gene product, or sequence. Such sequences include "mutant" sequences, or sequences in which the biological activity is altered to some degree but retains at least some of the original biological activity.

Alternatively, DNA analog sequences are "substantially identical" to specific DNA sequences disclosed herein if: (a) the DNA analog sequence is derived from coding regions of the natural enzyme gene; or (b) the DNA analog sequence is capable of hybridization of DNA sequences of (a) under stringent conditions and which encode biologically active enzyme gene products; or (c) the DNA sequences are degenerate as a result of alternative genetic code to the DNA analog sequences defined in (a) and/or (b). Substantially identical analog proteins will be equal to or greater than about 60%, 70%, 80%, 90%, 95%, 96%, 97%, 98%, or 99% identical to the corresponding sequence of the native protein. Sequences having lesser degrees of identity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Sequence identity or percent similarity of a DNA or peptide sequence can be determined, for example, by comparing sequence information using the GAP computer program, available from the University of Wisconsin Geneticist Computer Group. The GAP program utilizes the alignment method of Needleman et al. (1970) *J Mol Biol* 48:443, as revised by Smith et al. (1981) *Adv Appl Math* 2:482. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See Schwartz et al. (1979) *Nuc Acids Res* 6(2):745-755; Gribskov et al. (1986) *Nuc Acids Res* 14(1):327-334.

In certain embodiments, the present subject matter concerns the use of the enzyme genes and gene products that include within their respective sequences a sequence that is essentially that of an enzyme gene, or the corresponding protein. For example, the term "a sequence essentially as that of an OST gene", means that the sequence is substantially identical or substantially similar to a portion of an OST gene and contains a minority of bases or amino acids (whether DNA or protein) which are not identical to those of an OST protein or an OST gene, or which are not a biologically functional equivalent. The terms "a sequence essentially as that of an epimerase gene", "a sequence essentially as that of a glycosyl transferase gene", and "a sequence essentially as that of a heparosan synthase gene" have similar meanings. The term "biologically functional equivalent" is well understood in the art and is further defined in detail herein. Nucleotide sequences are "essentially the same" where they have between about 75% and about 85% or more preferably, between about 86% and about 90%, or more preferably greater than 90%, or more preferably between about 91% and about 95%, or even more preferably, between about 96% and about 99%; of nucleic acid residues which are identical to the nucleotide sequence of the enzyme gene. Similarly, peptide sequences which have about 60%, 70%, 80%, or 90%, or preferably from 90-95%, or more preferably greater than 96%, or more preferably 95-98%, or most preferably 96%, 97%, 98%, or 99% amino acids which are identical or functionally equivalent or biologically functionally equivalent to the amino acids of the enzyme polypeptide will be sequences which are "essentially the same".

Gene products and encoding nucleic acid sequences for the enzymes employed in the disclosed methods, which have functionally equivalent codons, are also covered by the presently disclosed subject matter. The term "functionally equivalent codon" is used herein to refer to codons that encode the same amino acid, such as the ACG and AGU codons for serine. Applicants contemplate substitution of functionally equivalent codons of Table 1 into sequences of the enzymes disclosed herein as equivalents.

TABLE 1

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic acid | Glu | E | GAA GAG |
| Phenylalanine | Phe | F | UUC UUU |

TABLE 1-continued

Functionally Equivalent Codons

| Amino Acids | | | Codons |
|---|---|---|---|
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood by those of skill in the art that amino acid and nucleic acid sequences can include additional residues, such as additional N- or C-terminal amino acids or 5' or 3' nucleic acid sequences, and yet still be encompassed by the enzymes disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present subject matter also encompasses the use of nucleotide segments that are complementary to the sequences of the present subject matter, in one embodiment, segments that are fully complementary, i.e. complementary for their entire length. Nucleic acid sequences that are "complementary" are those, which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

One technique in the art for assessing complementary sequences and/or isolating complementary nucleotide sequences is hybridization. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See e.g., Wethmur & Davidson (1968) *J Mol Biol* 31:349-370. Determining appropriate hybridization conditions to identify and/or isolate sequences containing high levels of homology is well known in the art. See e.g., Sambrook et al. (2001) *Molecular Cloning: A Laboratory Manual*, Third Edition, Cold Spring Harbor Laboratory Press, Cold Spring Harbor, N.Y.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C. Another example of "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68° C. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate).

Nucleic acids that are substantially identical to the provided enzymes, e.g., allelic variants, genetically altered versions of the gene, etc., bind to the disclosed OSTs under stringent hybridization conditions. By using probes, particularly labeled probes of DNA sequences, one can isolate homologous or related genes. The source of homologous genes can be any species, e.g., primate species, particularly human; rodents, such as rats and mice; canines; felines; bovines; ovines; equines; insects; yeasts; nematodes; etc.

Between mammalian species, e.g., human, mouse and rat, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides long, more usually at least about 30 nucleotides long, and can extend to the complete sequence that is being compared. Algorithms for sequence analysis are known in the art, such as BLAST, described in Altschul et al. (1990) *J Mol Biol* 215:403-410. The sequences provided herein are essential for recognizing enzymes related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position—these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine. When percentages are referred to herein, it is meant to refer to percent identity. The percent identities referenced herein can be generated by alignments with the program GENEWORKS™ (Oxford Molecular, Inc. of Campbell, Calif., U.S.A.) and/or the BLAST program at the NCBI website. Another commonly used alignment program is entitled CLUSTAL W and is described in Thompson et al. (1994) *Nucleic Acids Res* 22(22):4673-4680, among other places.

The term "gene" is used for simplicity to refer to a functional protein, polypeptide or peptide encoding unit. As will be understood by those in the art, this functional term includes both genomic sequences and cDNA sequences.

As noted above, modifications and changes can be made in the structure of enzyme proteins and peptides described herein and still constitute a molecule having like or otherwise desirable characteristics. For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the presently disclosed subject matter is not limited to a particular mechanism of action. It is thus contemplated in accordance with the present subject matter that various changes can be made in the sequence of the enzyme proteins and peptides or underlying nucleic acid sequence without appreciable loss of their biological utility or activity.

Biologically functional equivalent peptides, as used herein, are peptides in which certain, but not most or all, of the amino acids can be substituted. Thus, applicants contemplate substitution of codons that encode biologically equivalent amino acids as described herein into the sequences of the disclosed enzymes, but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test enzyme mutants in order to examine enzyme activity, or other activity at the molecular level.

Amino acid substitutions, such as those which might be employed in modifying enzyme proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those, which are within ±1 of the original value, are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those, which are within ±1 of the original value, are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that the presently disclosed subject matter is not limited to the particular nucleic acid and amino acid sequences of the enzymes disclosed herein, including sulfotransferases, epimerases, glycosyltransferases, and/or heprosan synthases. Recombinant vectors and isolated DNA segments can therefore variously include the enzyme polypeptide-encoding region itself, include coding regions bearing selected alterations or modifications in the basic coding region, or include larger polypeptides which nevertheless comprise the enzyme polypeptide-encoding regions or can encode biologically functional equivalent proteins or peptides which have variant amino acid sequences. Biological activity of an enzyme can be determined using techniques generally known in the art, for example as disclosed herein in the Examples.

The nucleic acid segments of the present subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of the enzymes disclosed herein, such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also contemplated to be useful.

Recombinant vectors form further aspects of the present subject matter. Particularly useful vectors are those in which the coding portion of the DNA segment is positioned under the control of a promoter. The promoter can be that naturally associated with an enzyme gene, as can be obtained by isolating the 5' non-coding sequences located upstream of the coding segment or exon, for example, using recombinant cloning and/or polymerase chain reaction (PCR) technology and/or other methods known in the art, in conjunction with the compositions disclosed herein.

In other embodiments, it is provided that certain advantages will be gained by positioning the coding DNA segment under the control of a recombinant, or heterologous, promoter. As used herein, a recombinant or heterologous promoter is a promoter that is not normally associated with an enzyme gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al. (2001) *Molecular Cloning: A Laboratory Manual*, Third Edition, Cold Spring Harbor Laboratory Press, Cold Spring Harbor, N.Y.). The promoters employed can be constitutive or inducible and can be used under the appropriate conditions to direct high level expression of the introduced DNA segment, such as is advantageous in the large-scale production of recombinant proteins or peptides.

In some embodiments of the method disclosed herein for sulfating polysaccharides, an enzyme of the presently disclosed subject matter (e.g. sulfotransferases, epimerases, glycosyltransferases, and/or heprosan synthases) can be immobilized on a substrate. This provides an advantage in that the substrate to which the enzymes are attached can be washed after a sulfation reaction to remove all components of the reaction except the bound enzymes. As such, the products of the reaction can be more easily separated from the enzymes catalyzing the reaction and the enzymes can be recycled and utilized again in multiple sulfation reactions. In some embodiments, the substrate is agarose. In particular embodiments, the agarose substrate is an agarose bead and the enzymes are linked to the beads.

III.B. Reduction of Inhibitory Effects of PAP

The presently disclosed methods for synthesizing heparin compounds can comprise the use of a PAPS regenerating enzyme and a sulfo donor compound. The PAPS regenerating enzyme catalyzes regeneration of the PAPS from the PAP utilizing the sulfo donor compound as a substrate. See, e.g., U.S. Pat. No. 6,255,088; and Burkart et al., (2000) J. Org. Chem. 65, 5565-5574, both of which are herein incorporated by reference in their entirety. Thus, the PAPS regeneration system provides the dual advantages of reducing the inhibitory effects of PAP accumulation on sulfotransferase activity while also constantly "recharging" the reaction mixture with the primary sulfo donor molecule, PAPS. In some embodiments, the PAPS regenerating enzyme is an estrogen sulfotransferase.

Thus, an aspect of the presently disclosed subject matter is directed to a sulfo donor compound (e.g., PAPS) regeneration process coupled with sulfation of a polysaccharide substrate. In particular, the process can be of a type wherein the sulfation of a polysaccharide substrate is catalyzed by a sulfotransferase, such as one or more OSTs, with a conversion of 3'-phosphoadenosine-5'-phosphosulfate (PAPS) to adenosine 3',5'-diphosphate (PAP). The sulfation process can be coupled with an enzymatic regeneration of the PAPS from the PAP. The enzymatic regeneration can employ an arylsulfotransferase as the catalyst and an aryl sulfate as a substrate. In some embodiments, the enzymatic regeneration can comprise a human or mouse estrogen sulfotransferase (EST). As disclosed elsewhere herein, preferred carbohydrate substrates can include GAGs, such as for example heparan sulfates, including heparin.

Coupling the sulfotransferase catalyzed sulfation reaction with a PAPS regeneration system can provide a further advantage of generating PAPS utilized in the reaction directly from PAP. That is, the reaction mixture can be formulated to combine PAP with a PAPS regenerating enzyme prior to or simultaneously with addition of a sulfotransferase to the reaction mixture. The PAPS regenerating enzyme can then generate PAPS from the PAP for use by the sulfotransferase, thereby alleviating the need of supplying any of the more expensive and unstable PAPS to the reaction mixture. For example, coupling the PAPS regeneration system to use PNPS as a sulfo donor can potentially reduce the cost of the synthesis of sulfated polysaccharides by as much as 1,000-fold. As such, in some embodiments of the presently disclosed subject matter a method of sulfating a polysaccharide is provided comprising providing a reaction mixture comprising therein adenosine 3',5'-diphosphate (PAP), a PAPS regenerating enzyme and a sulfo donor compound (other than PAPS, e.g., PNPS) and incubating the reaction mixture for a time period sufficient to catalyze the production of 3'-phosphoadenosine 5'-phosphosulfate (PAPS) from the PAP by the PAPS regenerating enzyme utilizing the sulfo donor compound as a substrate. The method further comprises incubating a polysaccharide substrate and at least one O-sulfotransferase (OST) enzyme with the reaction mixture, wherein production of a sulfated polysaccharide from the polysaccharide substrate is catalyzed by the OST enzyme with a conversion of the PAPS to PAP and wherein the PAPS regenerating enzyme then catalyzes regeneration of the PAPS from the PAP, again utilizing the sulfo donor compound as a substrate.

IV. Uses and Methods of Treatment for Ultra-Low Molecular Weight Heparins

Heparin compounds of the presently disclosed subject matter can comprise a synthetically sulfated polysaccharide possessing one or more structural and/or functional properties of heparan sulfates. Although exemplary embodiments of particular heparin compounds such as ULMW heparin constructs 1 and 2 have been disclosed herein, the presently disclosed subject matter is not intended to be limited to the disclosed examples, but rather heparin compounds include all comparable synthetically sulfated polysaccharides as would be apparent to one of ordinary skill. Indeed, one of ordinary skill in the art, upon a review of the instant disclosure, is capable of producing numerous heparin compounds based upon the disclosed methods and compounds.

Just as heparan sulfate regulates a wide range of physiologic and pathophysiologic functions, including blood coagulation, embryonic development, suppressing tumor growth, and controlling the eating behavior of test subjects by interacting with specific regulatory proteins, heparin compounds synthesized by the presently disclosed methods, e.g. ULMW heparin constructs 1 and 2, can be used to regulate the same biological processes. As would be appreciated by one of ordinary skill in the art, heparin constructs can be purposefully designed and synthesized using the disclosed methods to thereby produce compounds with unique sulfation patterns that dictate their biological activity and their subsequent utility as a therapeutic compound. By way of example and not limitation, heparin compounds synthesized by the presently disclosed methods can be used as a blood clotting agent to prevent blood clots, with particular uses in surgery and kidney dialysis, and for preventing venous thrombosis among high risk patients.

Heparin compounds synthesized by the presently disclosed methods, e.g. ULMW heparin constructs 1 and 2, can be administered to a subject in a therapeutically effective amount for the treatment of conditions as described above. An effective dose of a composition of the presently disclosed subject matter is administered to a subject in need thereof. A "therapeutically effective amount" is an amount of the composition sufficient to produce a measurable response (e.g., anticoagulation in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, and the condition and prior medical history of the subject being treated. However, it is within the skill of the art to start doses of the compositions at levels lower than required to achieve the desired therapeutic effect and to gradually increase the dosage until the desired effect is achieved.

The potency of a composition can vary, and therefore a "therapeutically effective" amount can vary. However, one skilled in the art can readily assess the potency and efficacy, e.g. anti-Xa activity, of a candidate composition of the presently disclosed subject matter and adjust the therapeutic regimen accordingly.

After review of the disclosure of the presently disclosed subject matter presented herein, one of ordinary skill in the art can tailor the dosages to an individual patient, taking into account the particular formulation, and method for administration to be used with the composition. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Materials and Methods for Examples 1-6

Expression of HS biosynthetic enzymes. A total of eight enzymes were used for the synthesis, including NST, $C_5$-epimerase ($C_5$-epi), 2-OST, 6-OST-1,6-OST-3,3-OST-1, N-acetyl glucosaminyl transferase of *E. coli* K5 (KfiA), and heparosan synthase-2 (pmHS2). All enzymes were expressed in *E. coli* and purified by appropriate affinity chromatography as described previously (Liu et al., 2010).

Preparation of enzyme cofactors. A sulfo donor, 3'-phosphoadenosine 5'-phophosulfate (PAPS), was prepared using adenosine phosphokinase and ATP-sulfurylase (Zhou et al., 2010). Preparation of UDP-GlcNTFA was completed using $GlcNH_2$-1-phosphate (Sigma, St. Louis, Mo., United States of America) and glucosamine-1-phosphate acetyltransferase/N-acetylglucosamine-1-phosphate uridyltransferase (GlmU) as described previously (Liu et al., 2010).

Preparation of oligosaccharide backbone. Referring to FIGS. 1A-1B, tetrasaccharide 2 (40 mg) was synthesized by using disaccharide 1, KfiA, pmHS2 and UDP-GlcNTFA and UDP-GlcUA as described previously (Liu et al., 2010). The product was purified by a Biogel® P-2 column (0.75×200 cm; BioRad, Hercules, Calif., United States of America) that was equilibrated with 0.1M ammonium bicarbonate at a flow rate of 6 ml/h. The fractions were then subjected to the analysis by electrospray ionization mass spectrometry (ESI-MS). Those fractions containing tetrasaccharide 4 were pooled. The procedures for synthesizing heptasaccharide 3 and hexasaccharide 4 were essentially the same. Using ESI-MS to locate the fractions containing products significantly improved the yield for the synthesis of oligosaccharides.

NMR analysis. Constructs 1 and 2 were analyzed by 1D $^1$H-NMR and 2D NMR ($^1$H-$^{13}$C HMQC, $^1$H-$^1$H COSY, TOCSY, and NOESY). All nuclear magnetic resonance (NMR) experiments were performed at 298 K on Bruker AVANCE™ II 800 MHz spectrometer (Bruker Daltonics, Inc., Billerica, Mass., United States of America) with TOP-SPIN™ 2.1 software (Bruker Daltonics, Inc.). Samples (3.0 to 6.0 mg) were each dissolved in 0.5 mL $D_2O$ (99.996%, Sigma, St. Louis, Mo., United States of America) and lyophilized three times to remove the exchangeable protons. The samples were re-dissolved in 0.4 mL $D_2O$ and transferred to NORRELL® NMR microtubes (OD 5 mm, Norrell, Landisville, N.J., United States of America). 1D $^1$H NMR experiments were performed with 256 scans and an acquisition time of 850 msec. 2D $^1$H-$^{13}$C Heteronuclear Multiple Quantum Coherence (HMQC) experiments were performed with 16 scans, 1.5 sec relaxation delay, and 250 msec acquisition time. 2D $^1$H-$^1$H correlation spectroscopy (COSY) experiments were performed with 16 scans, 1.5 sec relaxation delay, and 500 msec acquisition time. 2D $^1$H-$^1$H Total Correlation Spectroscopy (TOCSY) experiments were performed with 16 scans, 1.5 sec relaxation delay, and 850 msec acquisition time. 2D Nuclear Overhauser Effect Spectroscopy (NOESY) experiments were performed with 8 scans, 1.0 sec relaxation delay, 850 msec acquisition time, and 300 msec mixing time.

Determination of the anticoagulant activity in vivo. ULMW construct 1, ULMW construct 2 and ARIXTRA® were administered subcutaneously at a dose of 120 µg/kg to New Zealand white rabbits weighing from 2 to 5 kg. Rabbit blood samples were collected at 0, 0.5, 1, 2, 3, 6, 8 and 24 h from either the central auricular artery or the right common carotid artery via an inserted polyethylene tube (PE190). Insertion of PE tubing and subsequent blood sampling were performed under anesthesia induced and maintained by subcutaneous co-administration of ketamine (20 mg/kg) and xylazine (10 mg/kg). All blood samples were collected in 2-ml EPPENDORF® tubes (Eppendorf, Hamburg, Germany) containing 100 µl sodium citrate and plasma was immediately prepared by centrifugation at 3000×g for 10 min and stored at −20° C. until time of measurement of anti-Xa activity. The anti-Xa activity of plasma samples was measured directly on an ACL-8000 coagulation analyzer (Instrumentation Laboratory) using the HemosIL® Heparin kit (Beckman Coulter, Inc.).

Sulfation and epimerization modifications of oligosaccharide backbones. The conversion of hexasaccharide 3 to ULMW heparin construct 1 involved five steps, including detrifluoroacetylation/N-sulfation, $C_5$-epimerization/2-O-sulfation, 6-O-sulfation and 3-O-sulfation, as illustrated in FIGS. 1A-1B. Under one-pot reaction conditions, detrifluoroacetylated heptasaccharide 3 (3.5 mg) was incubated with reaction mixture containing 400 µM PAPS, 50 mM MES, pH 7.0, and 0.03 mg/ml NST in a total volume of 40 ml at 37° C. overnight. Then reaction mixture was diluted 3 times with 50 mM MES buffer to the total volume of 120 ml. To the reaction, the final concentrations of 0.03 mg/ml $C_5$-epi and 2 mM $CaCl_2$ were added. After incubating 30 min at 37° C., 2-OST 0.03 mg/ml, PAPS 400 µM was added in total 130 ml for additional overnight at 37° C. Then reaction mixture was diluted 3 times to total volume of 390 ml containing 400 µM PAPS, 50 mM MES, pH 7.0, and 0.03 mg/ml 6-OST1 and 0.03 mg/ml 6-OST3 for additional overnight at 37° C. Then 0.03 mg/ml 3-OST1, 10 mM $MnCl_2$, 5 mM $MgCl_2$, and PAPS at final concentration 600 µM was added in total 400 ml for additional overnight at 37° C. The product was purified by a DEAE column. The synthesis of ULMW heparin construct 2 followed essentially the same procedures.

An aliquot 1 ml of the large reaction mixture was combined with [$^{35}$S]PAPS (2×10$^6$ cpm, 0.2 nmol) to monitor the completion of each sulfation step. The reaction mixture was sampled every 6 h for the analysis by DEAE-HPLC and PAMN-HPLC to monitor progression of the reaction by observing emerge of the $^{35}$S-labeled product. After overnight incubation, an aliquot 0.5 ml of cold large scale reaction was subjected to further sulfation using 400 ug fresh enzyme, [$^{35}$S]PAPS (2×10$^6$ cpm, 50 uM), in total 2 ml for 4 h at 37° C. The sample was analyzed by DEAE-HPLC and PAMN-HPLC. If the large reaction was completed, no further $^{35}$S-labeled product could be observed. At this point, the next sulfation reaction mixture was added for new step reaction.

Mass spectrometric analysis of oligosaccharides. The analyses were performed using a Thermo LCQ-Deca (Thermo Scientific, Waltham, Mass., United States of America). The nonsulfated oligosaccharide (1 µl) eluted from BioGel P-2 was directly diluted in 200 µl of 9:1 MeOH/$H_2O$. A syringe pump (Harvard Apparatus) was used to introduce the sample via direct infusion (35 µl/min). Experiments were carried out in negative ionization mode with the electrospray source set to 5 KV and 275° C. Sulfated oligosaccharide (1 µl) was diluted in a different working solution containing 200 µl of 70% acetonitrile and 10 mM imidazole. Experiments for sulfated oligosaccharides were carried out in negative ionization mode with the electrospray source set to 2 KV and 200° C. The automatic gain control was set to 1×10$^7$ for full scan MS. The MS data were acquired and processed using Xcalibur 1.3.

Inhibition effect of the ULMW heparin compounds on the activity of factor Xa. Assays were based on a previously published method (Zhang et al., 2001; Duncan et al., 2004). Briefly, bovine factor Xa (Sigma, St. Louis, Mo., United States of America) was diluted to 5 U/ml with PBS containing 1 mg/ml BSA. Human AT (Cutter Biological) was diluted with PBS containing 1 mg/ml BSA to give a stock solution at the concentration of 27 µM. The chromogenic substrates, S-2765 was from Diapharma and made up at 1 mM in water. The oligosaccharide (ARIXTRA® synthetic ULMW heparin pentasaccharide, ULMW heparin construct 1 and 2) was dissolved in PBS at various concentrations (0.5 to 50 nM). The reaction mixture, which included 25 µl of AT stock solution and 25 µl of the solution containing the sample, was incubated at 37° C. for 2 min. Factor Xa (25 µl) was added. After incubating 37° C. for 4 min, 25 µl of S-2765 was added. The absorbance of the reaction mixture was measured at 405 nm continuously for 10 min. The absorbance values were plotted against the reaction time. The absorbance of the reaction mixture was measured at 405 nm continuously for 10 min. The initial reaction rates as a function of concentration were used to calculate the $IC_{50}$ values.

HPLC analysis. Both DEAE-HPLC and polyamine-based anion exchange (PAMN)—HPLC were used to purify the oligosaccharides. The elution conditions for the HPLC analysis were described elsewhere (Liu et al., 2010).

Determination of the binding of ULMW heparin construct 1 and 2 to antithrombin (AT) by affinity coelectrophoresis. The dissociation constant ($K_d$) of each sample and AT was determined using affinity co-electrophoresis (Lee & Lander, 1991). Approximately 4000-5000 cpm of antithrombin-binding $^{35}$S-labeled ULMW heparin construct 1 or 2 was loaded per lane with zones of AT at concentrations 0, 4, 8, 16, 32, 60, 120, 240 and 500 nM. The gel was performed at 400 mA for 2 hours, dried and analyzed on a Phospholmager Storm 860 (Amersham Biosciences, Uppsala, Sweden). The retardation coefficient was calculated at $R=(M_0-M)/M_0$, where $M_0$ is the mobility of the polysaccharide through the zone without AT, and M is the mobility of the sample through each separation zone. The retardation coefficient was then plotted against the retardation coefficient divided by its respective concentration of AT. The slope of the line represents $-1/K_d$.

Example 1

Synthesis of Construct 1

The synthesis of ULMW heparins according to the presently disclosed subject matter can include backbone elongation and saccharide modification (FIGS. 1A and 1B). Referring to FIGS. 1A and 1B, disaccharide 1 was utilized as the starting material and glycosyl acceptor. In some embodiments, a disaccharide was elongated by glycosyl transferases and it was prepared in multi-gram quantities from heparosan, readily obtained by fermentation. Elongation of disaccharide 1 to tetrasaccharide 2 was completed using two bacterial glycosyl transferases, N-acetyl glucosaminyl transferase of *E. coli* K5 (KfiA; Chen et al., 2006) and heparosan synthase-2 (pmHS2) from *Pasteurella multocida* (Sismey-Ragatz et al., 2007). In some embodiments, Tetrasaccharide 2 was designed with an unnatural monosaccharide, GlcNTFA (N-trifluoroacetyl glucosamine), since the N-TFA group can be readily converted to an N-sulfo group in a later step. Alternatively, in some embodiments any monosaccharide comprising a moiety that is readily converted to an N-sulfo group, as would be appreciated by one of ordinary skill in the art, can be employed without departing from the scope of the instant disclosure.

In preparing ULMW heparin construct 1, tetrasaccharide 2 was elongated to heptasaccharide 3 in three steps with an overall yield of about 80% (FIG. 1A, step a, b and c). Heptasaccharide 3 was converted to the final product by a series of chemoenzymatic reactions, including conversion of the GlcNTFA residue to GlcNS (FIG. 1A, steps d and e), epimerization and 2-O-sulfation (FIG. 1A, step f, here epimerization of GlcUA to IdoUA is accompanied by 2-O-sulfation using 2-OST to form an IdoUA2S at residue D), 6-O-sulfation (FIG. 1A, step g) and 3-O-sulfation (FIG. 1A, step h, the 3-O-sulfation occurred at the residue C). In approximately ten steps, the synthesis of construct 1 was completed in this representative embodiment. This synthesis yielded about 3.5 mg with about 45% overall yield. Selective epimerization/2-O-sulfation of residue D but not residue B (step f) can take advantage of known enzyme specificity, as residue D is flanked by two GlcNS residues. Similarly, in the 3-O-sulfation step (step h), 3-OST-1 can selectively add a 3-O-sulfo group to residue C but not to residue E, because the residue C is flanked by a GlcUA residue at its non-reducing end.

The conversion of heptasaccharide 3 to ULMW heparin construct 1 can be desirable to ensure that each modification was completed. For this purpose, small-scale reactions were carried out in parallel utilizing [$^{35}$S]PAPS to form the $^{35}$S-labeled intermediates and monitored by DEAE-HPLC, enabling the ability to anticipate the reagent concentrations and reaction times required in large-scale synthesis (FIG. 5).

FIGS. 5A, 5B and 5C depict DEAE-HPLC chromatograms of $^{35}$S-labeled intermediates during the preparation of ULMW heparin construct 1. FIG. 5A shows the N—[$^{35}$S] sulfo labeled N-sulfated heptasaccharide. The proposed structure is shown adjacent to FIG. 5A and at the top of the right column. FIG. 5B shows the 2-O—[$^{35}$S]sulfo labeled heptasaccharide after the incubation with a mixture of C$_5$-epi and 2-OST. The proposed structure of this intermediate is shown adjacent to FIG. 5B and in the middle of the right column. FIG. 5C shows the 6-O—[$^{35}$S]sulfo labeled heptasaccharide after modification by 6-OST-1 and 6-OST-3. The proposed structure of this intermediate is shown adjacent to FIG. 5C and at the bottom of the right column. The right column also indicates the reaction involved in the synthesis. The product after 6-O-sulfation was subjected to 3-O-sulfation to yield ULMW heparin construct 1. The elution profile of ULMW heparin construct 1 on DEAE-HPLC is shown in FIG. 2A.

Example 2

Synthesis of Construct 2

In a representative embodiment, two extra steps were used to add a GlcNS6S residue to the non-reducing end in the synthesis of ULMW heparin construct 2. Tetrasaccharide 2 was first converted to hexasaccharide 4, and the N-TFA groups were replaced by N-sulfo groups to afford hexasaccharide 5 (FIG. 1B). Hexasaccharide 5 was elongated to a heptasaccharide with a non-reducing end GlcNTFA (residue A). This heptasaccharide was treated by C$_5$-epi and 2-OST (FIG. 1B, step f) to place an IdoUA2S at residue D (FIG. 1B, step f) forming heptasaccharide 6. The introduction of a GlcNTFA residue at the non-reducing end was a control point in this synthesis as it can prevent the action of C$_5$-epi and 2-OST on the GlcUA, (residue B in step f). Heptasaccharide 6 can then be converted to ULMW heparin construct 2 in a sequential one-pot reaction format (FIG. 1B, step d, e, g, h). Ensuring that 6-O-sulfation completed was confirmed by carrying out a small scale reaction using [$^{35}$S]PAPS (FIG. 6). Employing this method provided for the synthesis of about 7.2 mg of ULMW heparin construct 2 in about 12 steps with an overall yield of about 37%.

FIGS. 6A and 6B depict DEAE-HPLC profiles of $^{35}$S-labeled intermediates during the preparation of ULMW heparin construct 2. FIG. 6A shows the DEAE-HPLC profile of N—[$^{35}$S]sulfo labeled heptasaccharide. The proposed structure is shown adjacent to FIG. 6A and at the top of the right column. FIG. 6B shows the 6-O-[$^{35}$S]sulfo labeled heptasaccharide after modification by 6-OST-1 and 6-OST-3. The proposed structure is shown adjacent to FIG. 6B and on the bottom of the right column. The product after 6-O-sulfation was subjected to 3-O-sulfation to yield ULMW heparin construct 2. The elution profile of ULMW heparin construct 2 on DEAF-HPLC is shown in FIG. 3A.

Example 3

Structural Analysis of Construct 1 and Construct 2

The structure of construct 1 can be confirmed by ESI-MS and one-dimensional (1D) and two-dimensional (2D) NMR analysis (see, e.g. FIGS. 2A-2D). FIGS. 2A-2D depict the results of structural characterization analysis of ULMW heparin construct 1. FIG. 2A shows the DEAE-HPLC profile of $^{35}$S-labeled product. FIG. 2B shows the ESI-MS spectrum of construct 1. Peaks 1, 2 and 3 represent the desulfated signals of the quadruply charged ion. Peaks 4, 5, 6 and 7 represent the desulfated signals of the triply charged ion. Peaks 8, 9, 10, 11 and 12 represent the desulfated signals of the doubly charged ion. FIG. 2C shows the 1D $^1$H NMR spectrum of ULMW construct 1. Peaks corresponding to the anomeric protons of the construct are clearly identifiable. FIG. 2D shows the 2D correlation spectroscopy (COSY) spectrum of construct 1 with the peak assignments of the anomeric protons identified.

The 3-O-[$^{35}$S]sulfo labeled construct 1 showed a single symmetric peak that was analyzed by a high resolution DEAE-HPLC column (FIG. 2A), demonstrating that the product was pure (in the large-scale reaction purity was confirmed by polyacrylamide gel electrophoresis, FIG. 7A).

The low resolution ESI-MS analysis revealed ULMW heparin construct 1 to have a molecular mass to be 1778.5±0.8 Da, which is identical to the calculated molecular mass (1778.5 Da) (FIG. 2B). High resolution ESI-MS was next performed (Thermo LTQ XL Orbitrap, Thermo Scientific, Bremen, Germany) for accurate mass measurement of construct 1. The [M-2H]$^{2-}$ value observed was 887.5313 (calc. 887.5324). 1D and 2D NMR analysis confirmed the structure of ULMW heparin construct 1 (FIGS. 2C and 2D). The 2D $^1$H NMR clearly demonstrates the presence of 6 anomeric protons (FIG. 2D) that resonate as doublets at δ 5.35 (d, J=2.94 Hz, 2H), 5.48 (d, J=3.23 Hz, 1H), 5.09 (broad doublet, 1H), 4.53 (d, J=8.11 Hz, 1H), 4.46 (d, J=8.07 Hz, 1H). The small coupling constants (~3 Hz) of the anomeric protons indicate an α-linkage, and the large coupling constants (~8 Hz) indicate a β-linkage. The presence of an internal IdoUA2S is clearly visible as indicated by a characteristic anomeric signal at δ 5.09 ppm that resonates at ~0.6 ppm downfield relative to the anomeric proton of GlcUA residues. Additional 2D NMR experiments allowed for the assignment of all the signals in the spectrum (Table 3).

The structure of ULMW heparin construct 2 was proven using the same methods (FIGS. 3A-3D and Table 4). FIGS. 3A-3D depict the results of structural characterization analysis of ULMW heparin construct 2. FIG. 3A shows the DEAE-HPLC profile of $^{35}$S-labeled product. FIG. 3B shows the ESI-MS spectrum of ULMW heparin construct 2. Peak 1 (m/z=288.6) represents the signal loss of one sulfo group of ULMW heparin construct 2 carrying six charges. Peak 2 (m/z=330.4) represents the signal loss of two sulfo groups of ULMW heparin construct 2 carrying five charges. The measured molecular mass for ULMW heparin construct 2 was 1817.1±0.3 Da, which is very close to the calculated one (1816.5 Da) and was confirmed by exact mass measurements using high resolution MS. FIG. 3C shows the 1D $^1$H NMR spectrum of ULMW heparin construct 2. Peaks corresponding to the anomeric protons of the construct are clearly identifiable. FIG. 3D shows the 2D COSY spectrum of ULMW heparin construct 2 with the peak assignments of the anomeric protons identified.

High resolution ESI-MS of construct 2 afforded a value observed for [M-2H]$^{2-}$ of 906.5047 (calc. 906.5056). The 3-O—[$^{35}$S]sulfo labeled construct 2 showed a single symmetric peak that was analyzed by a high resolution DEAE-HPLC column (FIG. 3A), demonstrating that the product was pure (in the large-scale reaction purity was confirmed by polyacrylamide gel electrophoresis, FIG. 7B).

Figure 10:
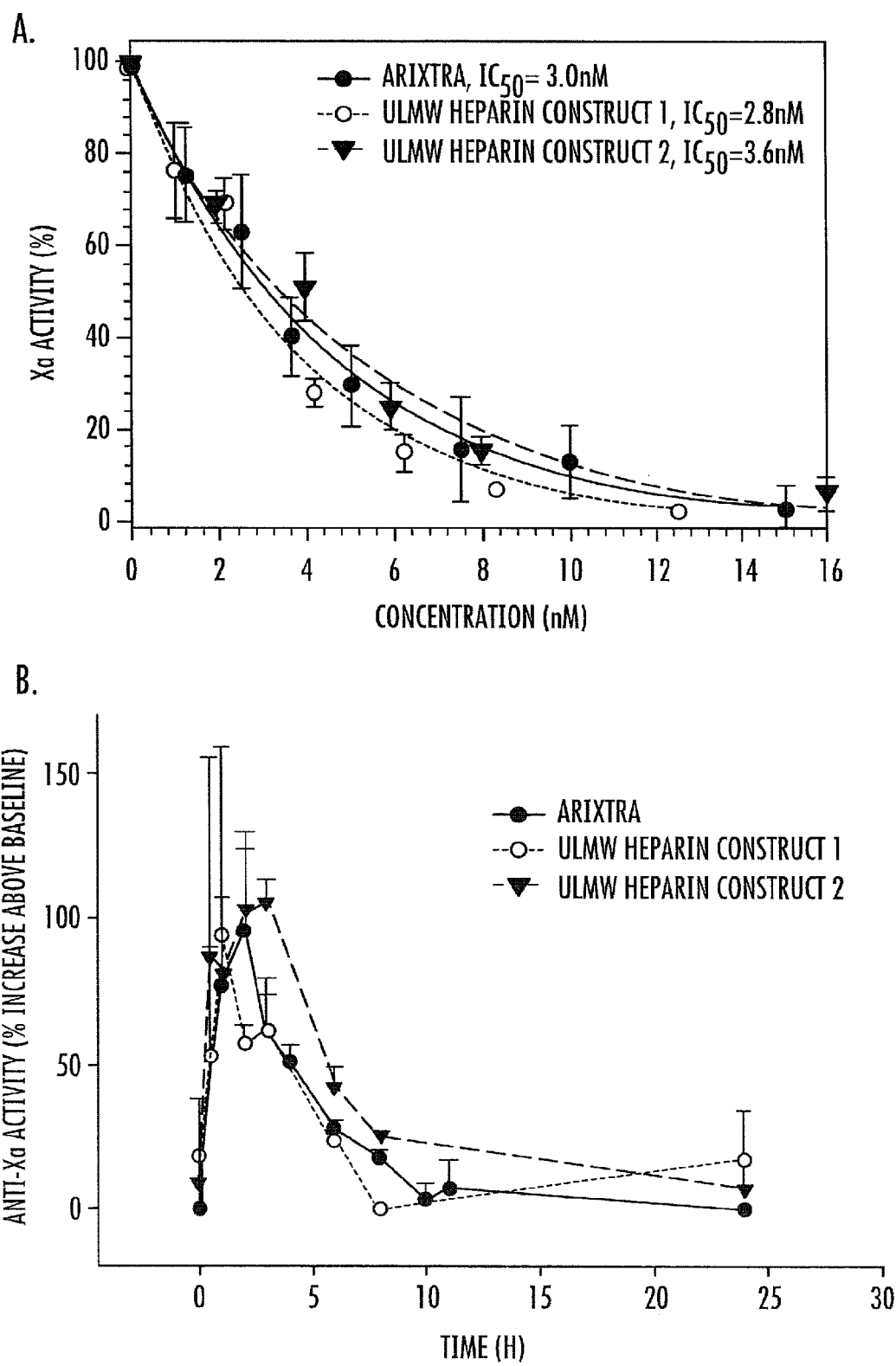
Figure 11:
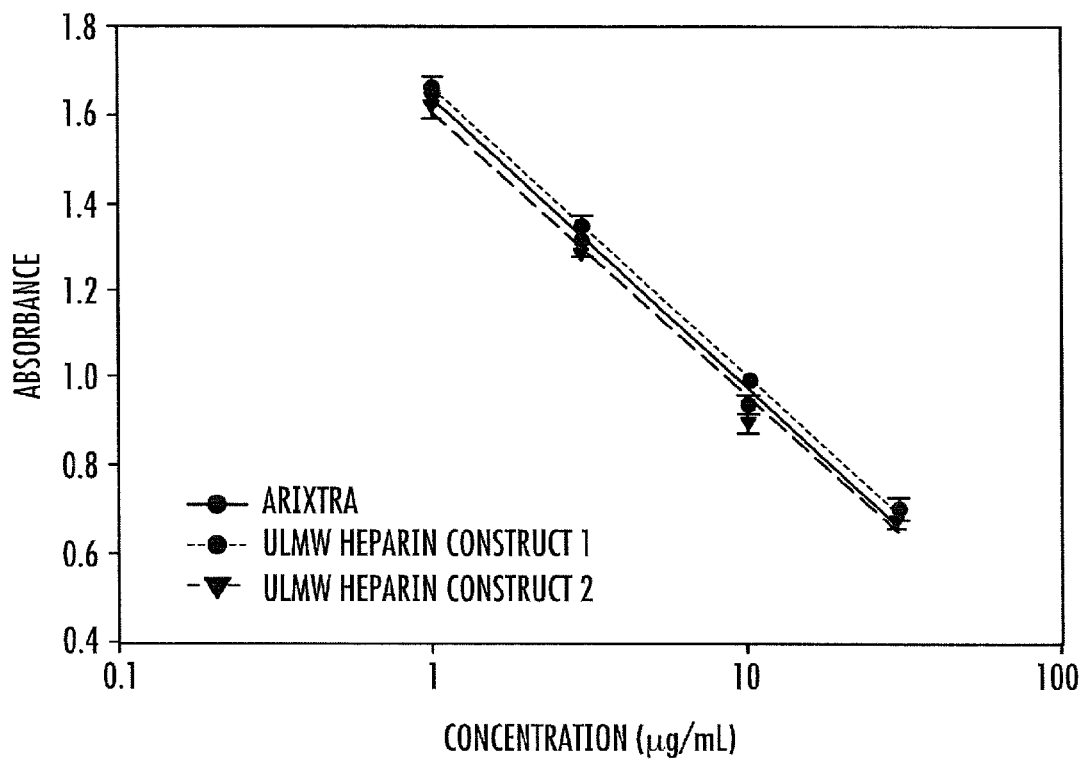

The $^1$H-$^{13}$C HMQC analysis for ULMW heparin constructs 1 and 2 further confirmed the assignments for NMR analysis (FIG. 8) and stock solutions of both were prepared at carefully determined concentrations for bioassays (FIG. 10). The structures of all intermediates were confirmed by ESI-MS analysis (Table 2).

FIGS. 7A and 7B are images of two polyacrylamide gels. The gels were subject to polyacrylamide gel electrophoresis (PAGE) for the assessment of the purity of ARIXTRA® and ULMW heparin constructs. ULMW heparin construct 1 was analyzed on the gel shown in FIG. 7A. ULMW heparin construct 2 was analyzed on the gel shown in FIG. 7B. Each analysis included the use of a 22% PAGE gel on which was loaded 8 μg of bovine lung derived heparin oligosaccharide standards (left lane; Edens et al., 1992), 1.2 μg of ARIXTRA® (middle lane), and 1.2 μg of construct 1 (right lane of FIG. 7A) or construct 2 (right lane of FIG. 7B), which was subjected to electrophoresis for 1.5 h at 200 V and fixed and stained with Alcian blue (Edens et al., 1992). The labeled bands in the standard ladder (left lane) were assigned using homogenous oligosaccharides.

TABLE 2

Summary of the ESI-MS analysis of intermediates and final products

| Oligosaccharides | Structures | Calculated MW (Da) | Measured MW (Da)[3] |
|---|---|---|---|
| Disaccharide 1 | GlcUA-AnMan[1] | 340.3 | 340.3 ± 0.2 |
| Tetrasaccharide 2[2] | GlcUA-GlcNH$_2$-GlcUA-AnMan[2] | 677.6 | 677.4 ± 0.1 |

TABLE 2-continued

Summary of the ESI-MS analysis of intermediates and final products

| Oligosaccharides | Structures | Calculated MW (Da) | Measured MW (Da)[3] |
|---|---|---|---|
| Heptasaccharide 3[2] | GlcNAc-GlcUA-GlcNH$_2$-GlcUA-GlcNH$_2$-GlcUA-AnMan | 1218.0 | 1218.2 ± 0.4 |
| Hexasaccharide 4[2] | GlcUA-GlcNH$_2$-GlcUA-GlcNH$_2$-GlcUA-AnMan | 1014.8 | 1015.1 ± 0.4 |
| Hexasaccharide 5 | GlcUA-GlcNS-GlcUA-GlcNS-GlcUA-AnMan | 1175.0 | 1175.4 ± 0.4 |
| Heptasaccharide 6 | GlcNTFA-GlcUA-GlcNS-IdoUA2S-GlcNS-GlcUA-AnMan | 1512.2 | 1512.2 ± 0.4 |

[1]AnMan represents 2,5-anhydromannitol
[2]Only detrifluoroacetylated products were analyzed by ESI-MS a mixture of the products carrying trifluoroacetyl groups and detrifluoroacetylated oligosaccharides were obtained. To simplify the MS analysis, all the samples were subject to complete detrifluoroacetylation before the analysis.
[3]Measured molecular weight (MW) was determined based on the average of the molecular ions carrying different charge states (average ± S.D.).

TABLE 3

$^1$H NMR chemical shift assignments (in ppm) of construct 1

| Residue | Proton | | | | | | |
|---|---|---|---|---|---|---|---|
| | 1 | 2 | 3 | 4 | 5 | 6a | 6b |
| A | 5.35 | 3.83 | 3.65 | 3.50 | 3.82 | 4.08 | 4.29 |
| B | 4.52 | 3.28 | 3.61 | 3.72 | 3.72 | — | — |
| C | 5.48 | 3.36 | 4.23 | 3.89 | 4.08 | 4.18 | 4.41 |
| D | 5.09 | 4.22 | 4.06 | 4.07 | 4.73 | — | — |
| E | 5.49 | 3.21 | 3.56 | 3.69 | 3.88 | 4.13 | 4.39 |
| F | 4.46 | 3.31 | 3.76 | 3.73 | 3.70 | — | — |
| G | 3.62/3.69* | 3.86 | 4.17 | 4.08 | 4.00 | 3.65 | 3.69 |

*Ring G (the reducing end residue) has 2 protons on C-1

TABLE 4

$^1$H NMR chemical shift assignments (in ppm) of construct 2

| Residue | Proton | | | | | | |
|---|---|---|---|---|---|---|---|
| | 1 | 2 | 3 | 4 | 5 | 6a | 6b |
| A | 5.50 | 3.18 | 3.52 | 3.51 | 3.74 | 4.07 | 4.27 |
| B | 4.55 | 3.33 | 3.76 | 3.85 | 3.78 | — | — |
| C | 5.47 | 3.36 | 4.25 | 3.90 | 3.99 | 4.19 | 4.39 |
| D | 5.12 | 4.22 | 4.10 | 4.10 | 4.88 | — | — |
| E | 5.49 | 3.18 | 3.58 | 3.58 | 3.85 | 4.13 | 4.37 |
| F | 4.48 | 3.33 | 3.76 | 3.76 | 3.78 | — | — |
| G | 3.61/3.68* | 3.86 | 4.16 | 4.16 | 4.00 | 3.65 | 3.69 |

*Ring G (the reducing end residue) has 2 protons on C-1.

Example 4

Concentrations of Construct 1 and Construct 2

FIGS. 9A and 9B are histograms depicting the concentrations of ULMW heparin constructs 1 and 2 used in activity studies. For construct 1, shown in FIG. 9A, CH$_3$CD$_2$OH in D$_2$O (5 mM) was prepared at 0° C. by weighing 1.2 mg of CH$_3$CD$_2$OH and diluting to 5 mL. ULMW heparin construct 1 was dissolved in 335 μL of the 5 mM solution of CH$_3$CD$_2$OH in D$_2$O. The peak at ~1.0 ppm corresponds to the methyl group in CH$_3$CD$_2$OH, whereas the peak at ~2.0 ppm corresponds to the methyl group in N-acetyl. Taking the integration of these two peaks, the amount of construct 1 was calculated as: (3.45/3.00)×5 mM×335 µL×1778.48 g/mol=3.38 mg. For construct 2, shown in FIG. 9B, $CH_3CD_2OH$ in $D_2O$ (5 mM) was prepared at 0° C. by weighing 1.2 mg of $CH_3CD_2OH$ and diluting to 5 mL. ULMW heparin construct 2 was dissolved in 350 µL of the 5 mM solution of $CH_3CD_2OH$ in $D_2O$. The peak at ~1.0 ppm corresponds to the methyl group in $CH_3CD_2OH$, whereas the peak at ~3.4 ppm corresponds to the H-2 of ring B, C and F. Taking the integration of these two peaks, the amount of construct 2 was calculated as: (3.00/1.53)×5 mM×350 µL×1816.50 g/mol=6.23 mg. The two samples were dried, dissolved in water and transferred to Eppendorf tubes to prepare two stock solutions of construct 1 and construct 2 at 10 mg/mL for use in subsequent activity studies. The amount of construct 1 and 2 were also checked by carbazole assay against a heparin standard curve and were 3.95 (±0.05) mg and 7.17 (±0.75) mg, respectively (Bitter & Muir, 1992). The concentrations of constructs 1 and 2 determined by NMR were used in all of the activity studies (see Examples 5 and 6).

Example 5

Anticoagulant Activity of Construct 1 and Construct 2

The in vitro and in vivo anticoagulant activities of both ULMW heparin construct 1 and 2 were assessed and compared to ARIXTRA® synthetic ULMW heparin pentasaccharide. These ULMW heparins can exhibit anticoagulant activity by forming a 1:1 complex with AT, which subsequently inactivates factor Xa in the blood coagulation cascade (Weitz, 2005).

FIGS. 10A and 10B are histograms depicting the determination of the anticoagulant activities of ULMW heparin constructs 1 and 2.

FIG. 10A shows the anti-Xa activity using a chromogenic substrate. ARIXTRA® synthetic ULMW heparin pentasaccharide, construct 1 and construct 2 were incubated with antithrombin (AT), factor Xa and the peptide substrate. The activity of Xa was determined by the rate of the increase of the absorbance at 405 nm. The activity without drugs was defined as 100%. Each data point represents the average of four determinations ±S.D.

The binding affinity of AT to ULMW heparin construct 1 and 2 were 5.2±0.2 nM and 9.1±0.2 nM, respectively, which is similar to the value of 5.9±1.5 nM measured for ARIXTRA® synthetic ULMW heparin pentasaccharide. Next, the in vitro anti-Xa activity of each ULMW heparin was determined (Chen et al., 2005), the results of which are provided in FIG. 10A. The $IC_{50}$ value of ULMW heparin construct 1 and 2 was 2.8 nM and 3.6 nM, respectively, again similar to the 3.0 nM measured for ARIXTRA® synthetic ULMW heparin pentasaccharide.

Finally, the anticoagulant effect of each ULMW heparin was examined in vivo using a rabbit model (Mousa, 2010a; Mousa, 2010b). As illustrated in FIG. 10B, ARIXTRA® synthetic ULMW heparin pentasaccharide, construct 1 and construct 2 were each independently administered subcutaneously at 120 µg/kg to three rabbits (n=3) and plasma samples were collected from 0 to 24 h. The anti-Xa activity of plasma samples was measured against a standard curve (FIG. 11). The area under the curve (AUC) for ARIXTRA® synthetic ULMW heparin pentasaccharide, construct 1 and construct 2 were 457, 473 and 802, respectively. Error bars indicate the standard deviation. The pharmacodynamic (PD) profiles of ARIXTRA® synthetic ULMW heparin pentasaccharide, ULMW construct 1 and ULMW construct 2 were very similar (FIG. 10B).

FIG. 11 is a line graph of the in vitro assay method and standard curve for pharmacodynamic (PD) studies. ULMW heparin construct 1, ULMW heparin construct 2, and ARIXTRA® stock solutions were prepared at different concentrations, covering the range between 1 and 30 µg/mL in phosphate buffered saline. All solutions contained 20% blank rabbit plasma. The anti-Xa activity was measured on an ACL-8000 coagulation analyzer (Instrumentation Laboratory, Bedford, Mass., United States) using the HemosiL® Heparin kit (Beckman Coulter, Inc., Indianapolis, Ind., United States) (Mousa, 2008; Mousa, 2010). ARIXTRA®, $y=-0.284\ln(x)+1.6318$, $R^2=0.9958$, construct 1, $y=-0.283\ln(x)+1.6578$, $R^2=0.9995$; and construct 2, $y=-0.278\ln(x)+1.5972$, $R^2=0.9891$.

Example 6

Construct 1 does not Bind PF4

Platelet factor 4 (PF4) binds to heparan sulfate and thereby decreases its anti-Xa activity. The binding of PF4 was compared between $^{35}$S-labeled heparan sulfate and $^{35}$S-labeled ULMW heparin construct 1. These $^{35}$S-labeled compounds were incubated with various concentrations of PF4 in phosphate buffered saline (PBS) solution at room temperature for 15 min. The mixture was then spotted on a nitrocellulose membrane. The membrane was washed with PBS three times. The amount of $^{35}$S-labeled compound bound to the membrane was measured by scintillation counting. As illustrated in FIG. 12, more than 50% of $^{35}$S-labeled heparan sulfate (similar to heparin) bound to PF4, while no detectable $^{35}$S-labeled ULMW construct 1 bound to PF4.

ULMW construct 2 is not expected to bind to PF4 as it has a chemical structure similar to that of ULMW construct 1. Furthermore, the minimum size required for a heparin oligosaccharide to bind to PF4 is octasaccharide (Maccarana, 1993). Both ULMW heparin construct 1 and 2 are heptasaccharides.

Next, assays were performed to determine the anti-Xa activity of heparin and ULMW construct 1 in the presence of PF4. ULMWH construct 1 or heparin was incubated in 70 µl PBS containing 0.1 mg/ml bovine serum albumin (BSA), 10 µL antithrombin (0.2 mg/mL in PBS), and 0-16 µL PF4 (0.45 mg/mL), for two minutes at room temperature. Ten microliters of Xa was then added, and after four minutes, 30 µL of chromogenic substrate S-2765 (1 mg/mL) (Chromogenix, Milano, Italy) was added to initiate the color change reaction. Sequential absorbance readings at 405 nm were started immediately using an ELx808 plate reader (BioTek, Winooski, Vt., United States of America). The rate of increased absorbance relative to the rate of a control sample was used to define Xa activity. Quantities of ULMW construct 1 and heparin having approximately 8% Xa activity in the absence of PF4 were used.

In the absence of PF4 both heparin and ULMW heparin construct 1 displayed anti-Xa activity, as illustrated by the low activity of Xa at 0 µg/ml of PF4 in FIG. 13. However, upon the addition of PF4 into the reaction the activity of Xa was increased for the heparin sample. This is because heparin bound to PF4 and lost its anti-Xa activity. In contrast, the Xa activity of ULMW heparin construct 1 remained constant upon the introduction of PF4 to the reaction and even as the concentration PF4 increased, confirming that PF4 does not bind to ULMW heparin construct 1.

REFERENCES

The references listed below as well as all references cited in the specification are incorporated herein by reference to the extent that they supplement, explain, provide a background for or teach methodology, techniques and/or compositions employed herein.

Aikawa et al., (1999) *J. Biol. Chem.* 274, 2690.
Aikawa, W-I., et al., (2001) *J. Biol. Chem.* 276, 5876-5882.
Alexander, C. M., et al., (2000) *Nat. Genet.* 25, 329-332.
Altschul et al. (1990) *J Mol Biol* 215, 403-410.
Balagurunathan, K., Lech, M. Z., Beeler, D. L., Wu, Z. L. & Rosenberg, R. D. Nat.
Bernfield, M., et al., (1999) *Annu. Rev. Biochem.* 68, 729-777.
Biotechnol. 21, 1343-1346 (2003).
Bitter, T. & Muir, H. M. Anal. Biochem. 4, 330-334 (1962).
Bowman et al., (1999) *Chem. Biol.* 6, R9-R22.
Burkart, M. D., Izumi, M., Chapman, E., Lin, C., and Wong, C. (2000) *J. Org. Chem.* 65, 5565-5574.
Capita, I., and Linhardt, R. J. (2002) *Angew. Chem. Int. Ed.* 41, 390-412.
Carfi, A., et al., (2001) *Mol. Cell* 8:169-179.
Chen, J. et al. J. Biol. Chem. 280, 42817-42825 (2005).
Chen, M., Bridges, A. & Liu, J. Biochemistry 45, 12358-12365 (2006).
Chen, J., Jones, C. L. & Liu, J. Chem Biol 14, 986-993 (2007).
Dooley (1998) *Chemico-Biol. Interact.* 109, 29.
Duncan, M. B., Chen, J., Krise, J. P. & Liu, J. Biochim Biophys Acta 1671, 34-43 (2004).
Edens, R. E. et al. J. Pharm Sci. 81, 823-827 (1992).
Esko, J. D., and Lindahl, U. (2001) *J. Clin. Invest.* 108:169-173.
Esko, J. D., and Selleck, S. B. (2002) *Annu. Rev. Biochem.* 71, 435-471.
Falany (1997) *FASEB J.* 11, 1-2.
Feyerabend et al. (2006) Nat. Chem. Biol. 2, 195-196.
Fukuta et al. (1998) *Biochim. Biophys. Act.* 1399, 57.
Gribskov et al. (1986) *Nuc Acids Res* 14(1), 327-334.
Guerrini, M. et al. Nat. Biotechnol. 26, 669-675 (2008).
Habuchi et al., (1998) *J. Biol. Chem.* 273, 9208.
Habuchi, H., et al., (2000) *J. Biol. Chem.* 275, 2859-2868.
Hirsh, J., O'Donnell, M. O. & Eikelboom, J. W. Circulation 116, 552-560 (2007).
Krummenacher, C., et al., (1999) *J. Virol.* 73, 8127-8137.
Kyte et al. (1982) *J Mol Biol* 157, 105.
Lee, M. K. & Lander, A. D. Proc. Natl. Acad. Sci. USA 88, 2768-2772 (1991).
Lindahl, U., et al., (1998) *J. Biol. Chem.* 273, 24979-24982.
Lindahl, U., Li, J., Kusche-Gullberg, M., Salmivirta, M., Alaranta, S., Veromaa, T., Linhardt, R. J. (2003) *J. Med. Chem.* 46, 2551-2564.
Liu, J., et al., (1996) *J. Biol. Chem.* 271, 27072-27082.
Liu, J., Shworak, N. W., Sinaÿ, P., Schwartz, J. J., Zhang, L., Fritze, L. M. S., and Rosenberg, R. D. (1999) *J. Biol. Chem.* 274, 5185-5192.
Liu, J., Shriver, Z., Blaiklock, P., Yoshida, K., Sasisekharan, R., and Rosenberg, R. D. (1999) *J. Biol. Chem.* 274, 38155-38162.
Liu, J., et al., (2002) *J. Biol. Chem.* 277, 33456-33467.
Liu, J., and Thorp, S. C. (2002) *Med. Res. Rev.* 22, 1-25.
Liu, J. & Pedersen, L. C. Microbiol. Biotechnol. 74, 263-272 (2007).
Liu, H., Zhang, Z. & Linhardt, R. J. Nat Prod Rep 26, 313-321 (2009).
Liu, R. et al. J Biol Chem 285, 34240-34249 (2010).
Loganathan, D., Wang, H. M., Mallis, L. M. & Linhardt, R. J. Biochemistry 29, 4362-4368 (1990).
M. Maccarana, and U. Lindahl, Mode of interaction between platelet factor 4 and heparin *Glycobiology,* 1993, 3, 271.
Mackman, N. Nature 451, 914-918 (2008).
Martinez-Gonzalez, J. & Rodriguez, C. Expert Rev. Cardiovasc. Ther. 8, 625-634 (2010).
Mazany et al., (1998) *Biochim. Biophys. Act.* 1407, 92.
Mousa, S. A. in Drug Discovery and Evaluation: Pharmacological assays (ed. Vogel, H.) 393-456 (Springer-Verlag Berlin, Heidelberg, N.Y., 2008).
Mousa, S. A. Meth Mol Biol 663, 1-28 (2010).
Mousa, S. A. I Meth Mol Biol 663, 1-28 (2010a).
Mousa, S. A. Meth Mol Biol 663, 29-107 (2010b).
Nastuk et al. (1998) *J. Neuroscience* 18, 7167.
Needleman et al. (1970) *J Mol Biol* 48, 443.
Noti, C. & Seeberger, P. H. Chemistry & Biology 12, 731-756 (2005).
Ong et al., (1998) *J. Biol. Chem.* 273, 5190.
Ouyang et al., (1998) *J. Biol. Chem.* 273, 24770.
Petitou, M., Jacquinet, J. C., Choay, J., Lormeau, J. C. & Nassr, M. (1989).
Petitou, M. & van Boeckel, C. A. A. Angew. Chem. Int. Ed. 43, 3118-3133 (2004).
Reizes, O., et al., (2001) *Cell* 106:105-116.
Rosenberg, R. D., et al., (1997) *J. Clin. Invest.* 99, 2062-2070.
Saeki et al. (1998) *J. Biochem.* 124, 55.
Sambrook et al. (2001) *Molecular Cloning: A Laboratory Manual*, Third Edition, Cold Spring Harbor Laboratory Press, Cold Spring Harbor, N.Y.
Schwartz et al. (1979) *Nuc Acids Res* 6(2), 745-755.
Shukla, D., et al. (1999) *Cell* 99, 13-22.
Shukla, D., and Spear, P. G. (2001) *J. Clin. Invest.* 108, 503-510.
Shworak, N. W., et al., (1997) *J. Biol. Chem.* 272, 28008-28019.
Sismey-Ragatz, A. E. et al. J. Biol. Chem. 282, 28321-28327 (2007).
Smith et al. (1981) *Adv Appl Math* 2, 482.
Thompson et al. (1994) *Nucleic Acids Res* 22(22), 4673-4680.
Tohu, M. et al. Clin Appl Thrombos Hemostas 10, 301-309 (2004).
U.S. Pat. No. 6,255,088.
U.S. Pat. No. 4,554,101.
Uchimura et al. (1998) *J. Biol. Chem.* 273, 22577.
Weitz, J. I. in Hematology: Basic principles and practice (eds. Hoffman, R. et al.) 2249-2267 (Elsevier, Philadelphia, Pa., 2005).
Weitz, J. I. & Linkins, L. A. Expert Opin. Investig. Drugs 16, 271-282 (2007).
Weitz, J. I. Thromb. Res. 125 (Suppl 2), S30-S35 (2010).
Wethmur & Davidson (1968) *J Mol Biol* 31, 349-370.
Willis, S. H., et al., (1998) *J. Virol.* 72, 5938-5947.
WuDunn, D., and Spear, P. G. (1989) *J. Virol.* 63, 52-58.
Yoshinari et al., (1998) *J. Biochem.* 123, 740.
Zhang, L. et al. J. Biol. Chem. 276, 42311-42321 (2001).
Zhang, Z. et al. J Am Chem Soc 130, 12998-13007 (2008).
Zhou, X., Chandarajoti, K., Pham, T. Q., Liu, R. & Liu, J. Glycobiology, in press (2010).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of synthesizing a heparin compound, comprising the following sequential steps while monitoring the steps:

providing a monosaccharide substrate comprising glucuronic acid;

elongating the monosaccharide substrate to a tetrasaccharide using enzymes N-acetyl glucosaminyl transferase and heparosan synthase-2, and substrates glucuronic acid (GlcUA) and N-trifluoroacetyl glucosamine (GlcNTFA), wherein the tetrasaccharide has the following structure:

2

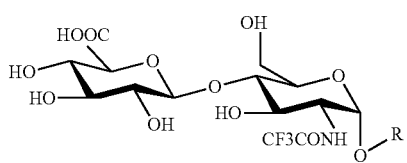

wherein R =

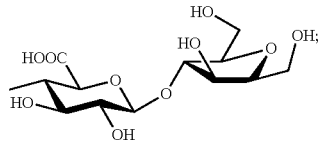

elongating the tetrasaccharide to a heptasaccharide using enzymes N-acetyl glucosaminyl transferase and heparosan synthase-2, and substrates glucuronic acid (GlcUA), N-trifluoroacetyl glucosamine (GlcNTFA), and N-acetylated glucosamine (GlcNAc), wherein the heptasaccharide has the following structure:

3

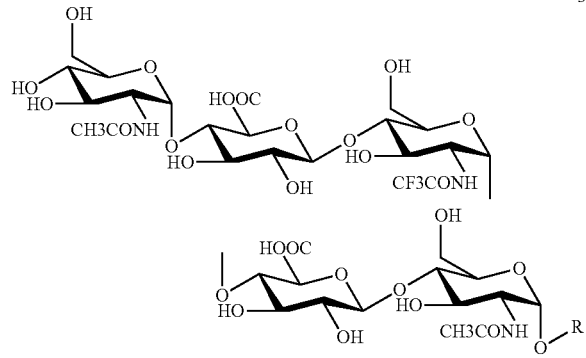

wherein R can be =

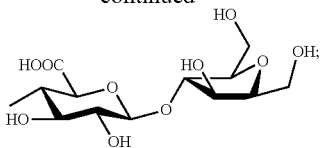

converting N-trifluoroacetyl glucosamine (GlcNTFA) residue(s) on the heptasaccharide to N-sulfo glucosamine (GlcNS) residues using N-sulfotransferase (NST), 3'-phosphoadenosine 5'-phosphosulfate (PAPS), triethylamine, CH$_3$OH, and H$_2$O;

epimerizing and sulfating the resultant heptasaccharide using C$_5$-epimerase (C$_5$-epi) and 2-O-sulfotransferase (2-OST) and 3'-phosphoadenosine 5'-phosphosulfate (PAPS);

sulfating the resultant heptasaccharide using 6-O-sulfotransferase-1 (6-OST-1) and 6-O-sulfotransferase-3 (6-OST-3) and 3'-phosphoadenosine 5'-phosphosulfate (PAPS);

sulfating the resultant heptasaccharide using 3-O-sulfotransferase-1 (3-OST-1) and 3'-phosphoadenosine 5'-phosphosulfate (PAPS); and purifying the resultant heptasaccharide to give a heparin compound, wherein the heparin compound is synthesized at a yield of greater than 30% and wherein the heparin compound is structurally homogeneous and has the following structure:

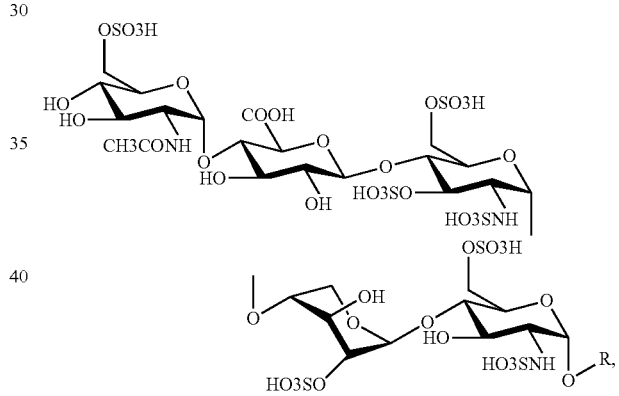

wherein R =

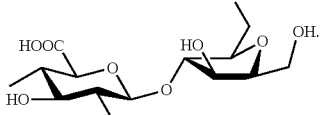

2. The method of claim 1, wherein the enzymes N-acetyl glucosaminyl transferase and heparosan synthase-2 are selected from the group consisting of N-acetyl glucosaminyl transferase of *E. coli* K5 (KfiA) and heparosan synthase-2 (pmHS2) from *Pasteurella multocida*.

3. The method of claim 1, wherein the method has a recovery yield about 400-fold higher than methods of chemically synthesizing heparin.

* * * * *